(12) United States Patent
Togawa et al.

(10) Patent No.: US 9,330,678 B2
(45) Date of Patent: May 3, 2016

(54) VOICE CONTROL DEVICE, VOICE CONTROL METHOD, AND PORTABLE TERMINAL DEVICE

(71) Applicant: FUJITSU LIMITED, Kawasaki-shi, Kanagawa (JP)

(72) Inventors: Taro Togawa, Kawasaki (JP); Chisato Ishikawa, Kawasaki (JP); Takeshi Otani, Kawasaki (JP); Masanao Suzuki, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 208 days.

(21) Appl. No.: 13/923,674

(22) Filed: Jun. 21, 2013

(65) Prior Publication Data
US 2013/0290002 A1 Oct. 31, 2013

Related U.S. Application Data

(63) Continuation of application No. PCT/JP2010/073609, filed on Dec. 27, 2010.

(51) Int. Cl.
*G10L 21/04* (2013.01)
*H04M 1/60* (2006.01)
*A61B 5/00* (2006.01)
*A61B 5/12* (2006.01)

(52) U.S. Cl.
CPC ............... *G10L 21/04* (2013.01); *A61B 5/0022* (2013.01); *A61B 5/123* (2013.01); *A61B 5/6898* (2013.01); *H04M 1/6025* (2013.01); *H04M 2250/74* (2013.01)

(58) Field of Classification Search
CPC .... A61B 5/0022; A61B 5/6898; G10L 21/04; G10L 25/78; H04M 1/6025
See application file for complete search history.

(56) References Cited

U.S. PATENT DOCUMENTS

| | | | |
|---|---|---|---|
| 4,377,158 A * | 3/1983 | Friedman et al. | 128/897 |
| 6,011,853 A | 1/2000 | Koski et al. | |
| 6,086,541 A * | 7/2000 | Rho | 600/559 |
| 6,212,496 B1 | 4/2001 | Campbell et al. | |
| 6,522,988 B1 * | 2/2003 | Hou | 702/122 |
| 7,198,605 B2 * | 4/2007 | Donofrio et al. | 600/559 |
| 2008/0027728 A1 * | 1/2008 | Luckett | 704/270 |

FOREIGN PATENT DOCUMENTS

| | | |
|---|---|---|
| CN | 101721214 | 6/2010 |
| EP | 0 697 780 | * 2/1996 |
| JP | 6-217398 | 8/1994 |

(Continued)

OTHER PUBLICATIONS

Patent Abstracts of Japan, Publication No. 07-066767, Published Mar. 10, 1995.

(Continued)

*Primary Examiner* — Angela A Armstrong
(74) *Attorney, Agent, or Firm* — Staas & Halsey LLP

(57) ABSTRACT

A voice control device includes a calculation section configured to calculate a response time representing a time difference between a voice in a received signal and a voice in a sending signal; a hearing estimate section configured to estimate hearing of a user based on the calculated response time; and a voice control section configured to control the received signal by a compensation quantity responsive to the estimated hearing.

10 Claims, 20 Drawing Sheets

(56) References Cited

FOREIGN PATENT DOCUMENTS

| JP | 7-66767 | 3/1995 |
|---|---|---|
| JP | 9-135194 | 5/1997 |
| JP | 10-126497 | 5/1998 |
| JP | 2000-165483 | 6/2000 |
| JP | 2006-38705 | 2/2006 |
| JP | 2006-165757 | 6/2006 |
| JP | 2006-345025 | 12/2006 |
| JP | 2008-311754 | 12/2008 |

OTHER PUBLICATIONS

Patent Abstracts of Japan, Publication No. 2006-038705, Published Feb. 9, 2006.
Patent Abstracts of Japan, Publication No. 06-217398, Published Aug. 5, 1994.
Patent Abstracts of Japan, Publication No. 2006-165757, Published Jun. 22, 2006.
Patent Abstracts of Japan, Publication No. 09-135194, Published May 20, 1997.
Patent Abstracts of Japan, Publication No. 10-126497, Published May 15, 1998.
Patent Abstracts of Japan, Publication No. 2000-165483, Published Jun. 16, 2000.
Patent Abstracts of Japan, Publication No. 2006-345025, Published Dec. 21, 2006.
Patent Abstracts of Japan, Publication No. 2008-311754, Published Dec. 25, 2008.
junokekka, "Hearing level Fiscal year 2001," http://www.hql.jp/project/funcdb2000/cyokaku/junon/junonkekka.htm, pp. 1-2 (2001).
Mako Katagiri et al., Technology Research Institute of Osaka Prefecture, "Age-related changes in human acuity of the right and left ears," http://tri-osaka.jp/group/infoele/life/sense/data/katagiri/070622.pdf, pp. 1.
Nagamine Mitsue, "Current state of neuroscientific study on decision making of senior citizens," http://www.caa.go.jp/seikatsu/keizaijikken/nousan2-1.pdf, Chapter 2, pp. 109-127.
Okayama, http://www.okayama.med.or.jp/ishi/bukai/h18kenshukai/05.pdf, pp. 4-7 (2006).
Toyko Hochouki, http://www.tokyo-hotyouki.co.jp/siryou.html, pp. 1.
International Search Report of PCT/JP2010/073609 mailed Mar. 15, 2011.
Espacenet English Abstract of Chinese Publication No. 101721214, Published Jun. 9, 2010.
Chinese Office Action dated Nov. 18, 2014 in corresponding Chinese Patent Application No. 201080070956.9.
Chinese Office Action dated Feb. 24, 2016 in corresponding Chinese Patent Application No. 201080070956.9.

\* cited by examiner

VOICE CONTROL DEVICE, VOICE CONTROL METHOD, AND PORTABLE TERMINAL DEVICE

CROSS-REFERENCE TO RELATED APPLICATIONS

This application is a continuation application of International Application PCT/JP2010/073609 filed on Dec. 27, 2010 and designated the U.S., the entire contents of which are incorporated herein by reference.

FIELD

The invention relates to a voice control device, a voice control method, a voice control program and a portable terminal device that control received sound.

BACKGROUND

Conventionally, there are portable terminal devices that execute control to make received voices easy to hear. For example, there is a technology with which multiple single-tone frequency signals are reproduced for a user to calculate the minimum hearing level based on the user's hearing result for processing a voice (Patent document 1).

Also, there is a technology with which if an operation signal is output that indicates a request for repetition of a guiding voice within a certain amount of time since the guiding voice has been output, the guiding voice is output again after adjusting a setting value designating output mode of the guiding voice (Patent document 2).

RELATED-ART DOCUMENTS

Patent Document

[Patent Document 1] Japanese Laid-open Patent Publication NO. 07-66767
[Patent document 2] Japanese Laid-open Patent Publication NO. 2006-38705

However, there is a problem with Patent document 1 in that it is not easy to use because a user needs to execute a hearing test that forces a complicated procedure upon the user. Also, there is a problem with Patent Document 2 in that a user needs to execute an operation to ask for repetition because the guiding voice is not adjusted if the operation to ask for repetition has not been executed.

SUMMARY

According to one embodiment, a voice control device includes a calculation section configured to calculate a response time representing a time difference between a voice in a received signal and a voice in a sending signal; a hearing estimate section configured to estimate hearing of a user based on the calculated response time; and a voice control section configured to control the received signal by a compensation quantity responsive to the estimated hearing.

The object and advantages of the embodiment will be realized and attained by means of the elements and combinations particularly pointed out in the claims. It is to be understood that both the foregoing general description and the following detailed description are exemplary and explanatory and are not restrictive of the invention as claimed.

DESCRIPTION OF EMBODIMENTS

First, a relationship between age and hearing will be described. Hearing is, for example, a minimum audible range.

Figure 1:
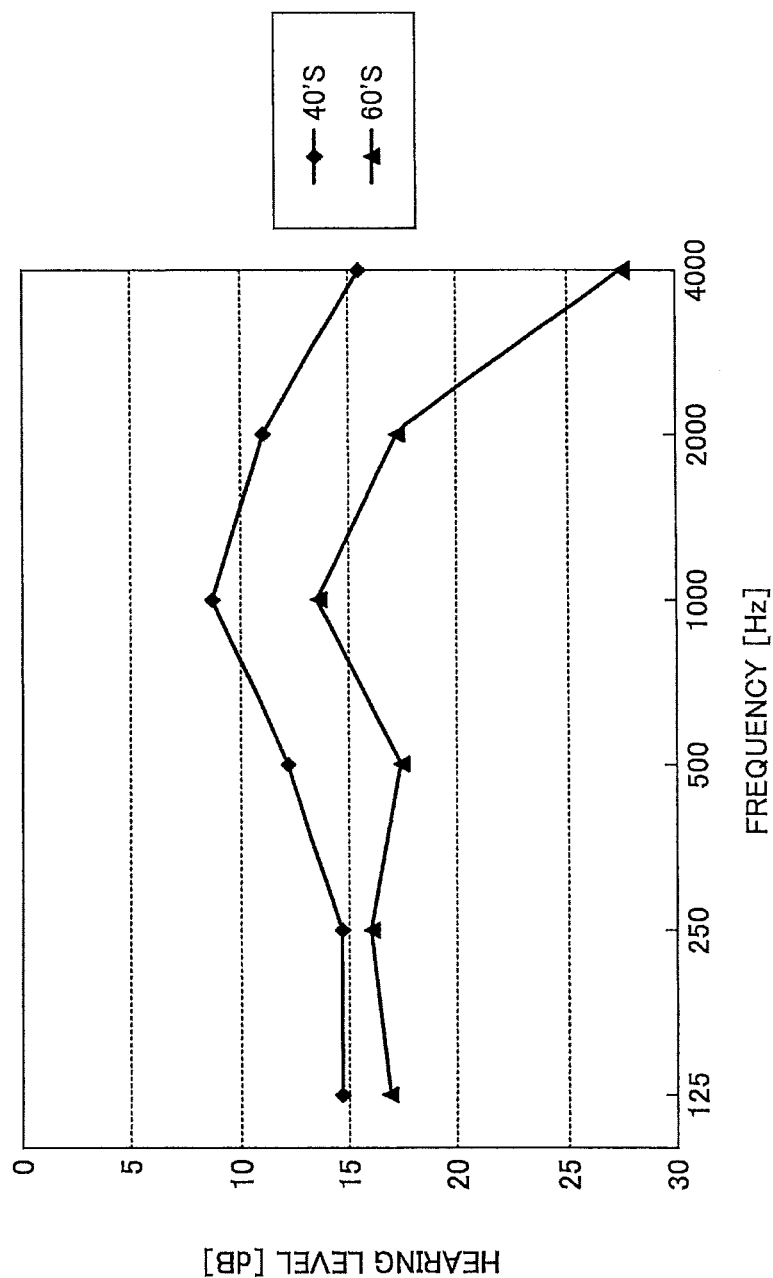
FIG. 1 is a schematic view illustrating a change of hearing level with aging.

FIG. 1 is a schematic view illustrating a change of hearing level with aging. According to an experiment illustrated in FIG. 1, it can be understood that there is a difference in the average hearing level between 40's and 60's. The hearing level of 60's notably drops in a high range (2 kHz to 4 kHz). Also, as for hearing impairment induced by aging, an investigation result was reported in
<http://tri-osaka.jp/group/infoele/life/sense/data/katagiri/070622.pdf>.

As illustrated in FIG. 1, it is already known that hearing level drops with aging. Especially, in a high frequency range, hearing level drops when one gets older.

Here, with aging, it is considered that hearing is impaired, information processing capability of the brain drops, and response time in a conversation gets slow. Refer, for example, to the second chapter of
<Http://www.caa.go.jp/seikatsu/keizaijikkennousan2-1.pdf>.

Thus, in the following, embodiments will be described in which response times during a telephone call is focused on, a user's hearing is estimated from response times, and a received voice is controlled in response to the estimated hearing to make the received sound easy to hear. In the following, the embodiments will be described with reference to the drawings.

First Embodiment

<Configuration>

Figure 2:
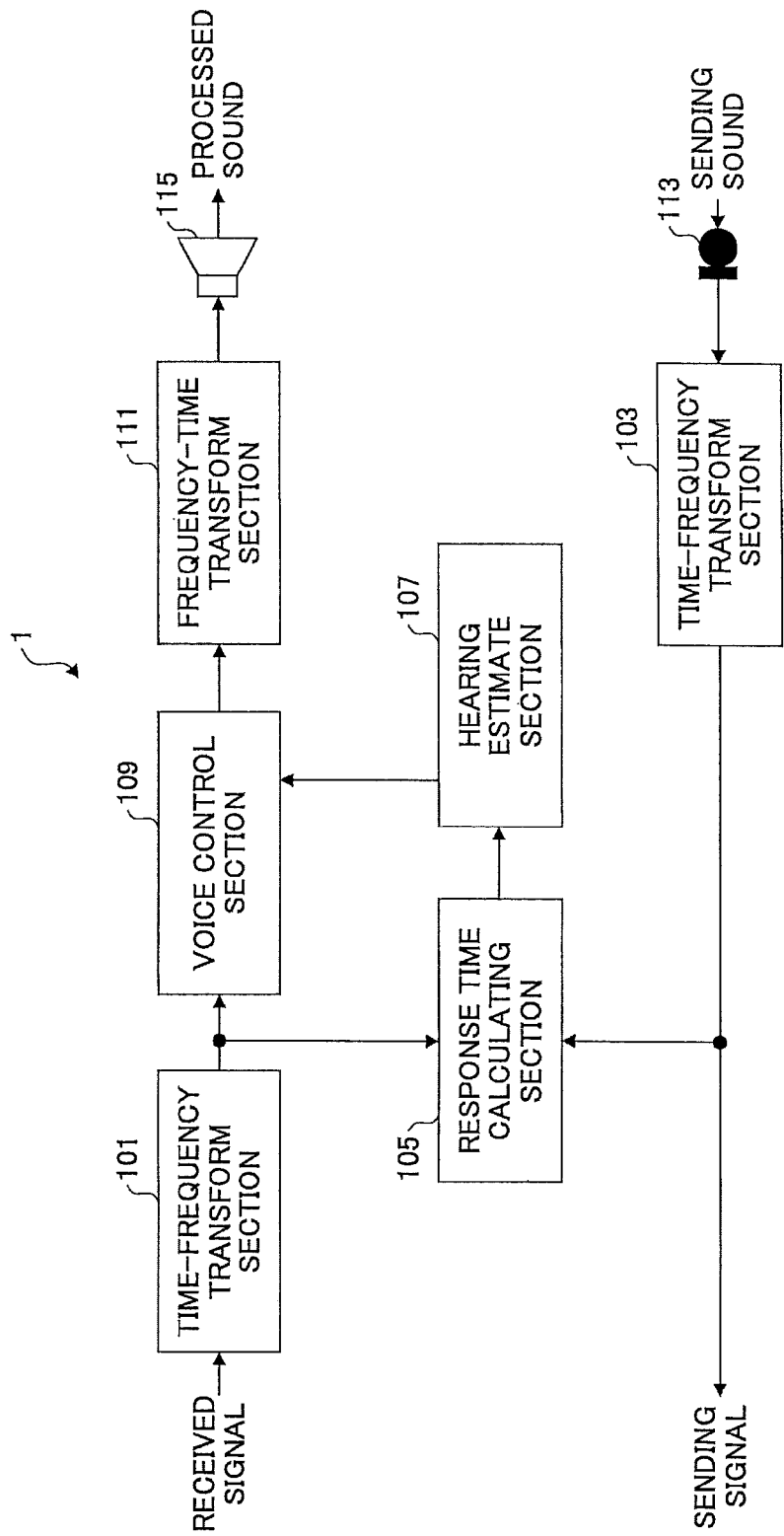
FIG. 2 is a block diagram illustrating an example of a configuration of a voice control device according to a first embodiment.

A configuration of a voice control device 1 will be described according to the first embodiment. FIG. 2 is a block diagram illustrating an example of a configuration of the voice control device 1 according to the first embodiment. As illustrated in FIG. 2, the voice control device 1 includes time-frequency transform sections 101 and 103, a response time calculating section 105, a hearing estimate section 107, a voice control section 109, and a frequency-time transform section 111.

The time-frequency transform section 101 transforms a received sound x into a received sound spectrum F(j) by executing a time-frequency transform according to the following formula (1). The time-frequency transform is, for example, a fast Fourier transform (FFT).

$$F(j) = \sum_{k=0}^{n-1} x_k e^{-\frac{2\pi i}{n} jk} \quad \text{formula (1)}$$

x: input signal
n: FFT analysis length (for example, 256)
j: frequency bin
k: Nyquist frequency The time-frequency transform section 101 outputs the obtained received sound spectrum to the response time calculating section 105 and the voice control section 109.

The time-frequency transform section 103 transforms a sending voice y input with a microphone 113 into a sending sound spectrum by similarly executing the time frequency transform according to the formula (1) described above. The time-frequency transform is, for example, a fast Fourier transform (FFT).

The time-frequency transform section 103 outputs the obtained sending sound spectrum to the response time calculating section 105.

Figure 3:
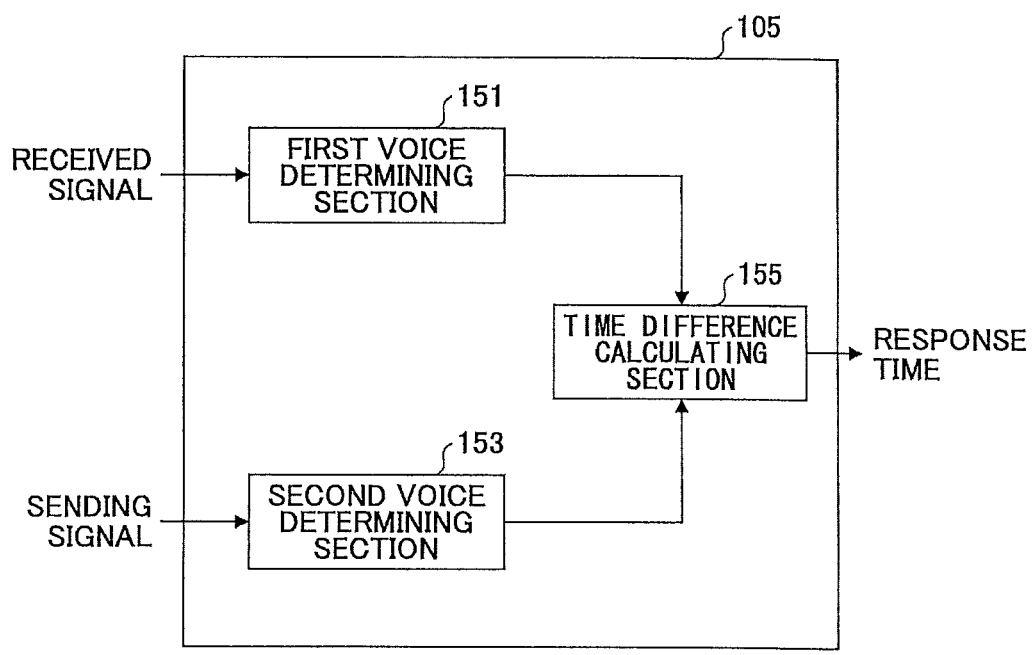
FIG. 3 is a block diagram illustrating an example of a configuration of a response time calculating section according to the first embodiment.

The response time calculating section 105 calculates a response time representing a time difference between the received signal and the sending signal. FIG. 3 is a block diagram illustrating an example of a configuration of the response time calculating section 105 according to the first embodiment. In the example illustrated in FIG. 3, the response time calculating section 105 includes a first voice determining section 151, a second voice determining section 153, and a time difference calculating section 155.

The first voice determining section 151 determines whether a received signal is voice or non-voice, which is received in units of frames including mixed voice and noise. The first voice determining section 151 may determine voice or non-voice using a publicly known technology.

For example, in Japanese Patent No. 3849116, voice or non-voice is determined for each frame of a input signal, based on a first voice characterizing quantity calculated using electric power, a zero crossing rate, a peak frequency of power spectrum, pitch cycle, etc., and a second voice characterizing quantity calculated based on a difference of peak frequency of power spectrum only in high order components.

The first voice determining section 151 outputs a determination result about voice or non-voice of the received signal to the time difference calculating section 155.

The second voice determining section 153 determines whether a sending signal is voice or non-voice, which is received in units of frames including mixed voice and noise. The second voice determining section 153 may determine voice or non-voice using a publicly known technology as in the first voice determining section 151. The second voice determining section 153 outputs a determination result about voice or non-voice of the sending signal to the time difference calculating section 155.

The time difference calculating section 155 calculates a time difference between an ending time of a voice segment in a received signal and a starting time of a voice segment in a sending signal, as a response time. The time difference calculating section 155 outputs the calculated response time to the hearing estimate section 107.

Figure 4:
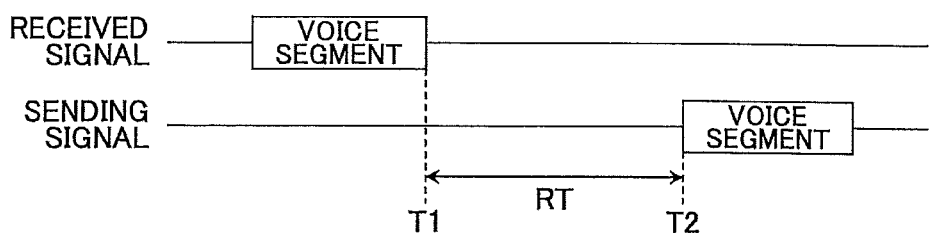
FIG. 4 is a schematic view illustrating a response time.

FIG. 4 is a schematic view illustrating the response time. In an example illustrated in FIG. 4, the time difference calculating section 155 calculates a response time RT by the following formula (2) using an ending time T1 of a voice segment in a received signal and a starting time T2 of a voice segment in a sending signal.

$$RT = T2 - T1 \quad \text{formula (2)}$$

Figure 5:
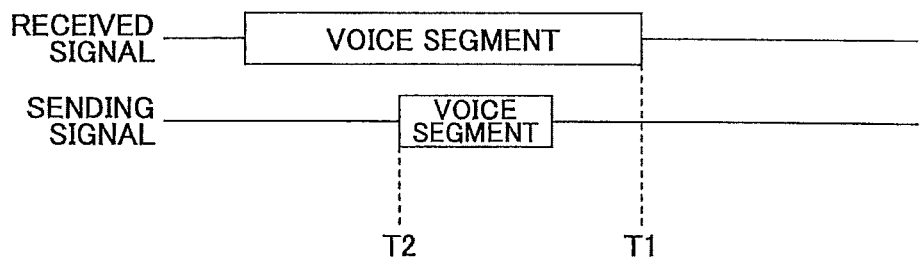
FIG. 5 is a schematic view illustrating an exception of the response time.

FIG. 5 is a schematic view illustrating an exception of the response time. In an example illustrated in FIG. 5, the time difference calculating section 155 does not calculate a response time if a starting time T2 of a voice segment in a sending signal is earlier than an ending time T1 of a voice segment in a received signal (T2<T1). This makes it possible to exclude cases where a received voice and a sending voice are overlapped due to a back channeling or the like.

A method for obtaining a response time is not limited to the example described above, but the response time calculating section 105 may simply use volume of a sending sound and volume of a received sound for recognizing a voice if the volume is greater than a predetermined threshold value to calculate a response time. The response time calculating section 105 may use a parameter for a received signal and a parameter for a sending signal to calculate a response time.

Returning to FIG. 2, the hearing estimate section 107 obtains the response time from the response time calculating section 105 to estimate a user's hearing from the response time. The hearing estimate section 107 holds information in which a response time and a hearing characteristic (for example, a minimum audible value) are associated, with which the minimum audible value is identified that is associated with the obtained response time.

Figure 6:
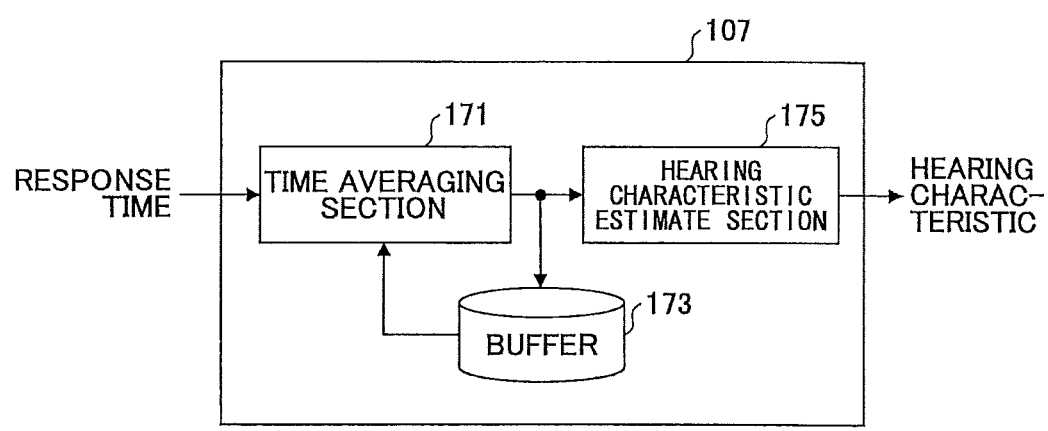
FIG. 6 is a block diagram illustrating an example of a configuration of a hearing estimate section of estimating hearing from the average value of response times according to the first embodiment.

Also, the hearing estimate section 107 may obtain the minimum audible value from the average value of response times. FIG. 6 is a block diagram illustrating an example of a configuration of the hearing estimate section 107 if estimating hearing from the average value of response times according to the first embodiment.

In an example illustrated in FIG. 6, the hearing estimate section 107 includes a time averaging section 171, a buffer 173, and a hearing characteristic estimate section 175. The time averaging section 171 calculates the average response time in which response times are averaged in time direction. The buffer 173 stores the past average response time.

The time averaging section 171 calculates the average response time, for example, by the following formula.

$$AVE\_RT = RT*COEF + AVE\_RT\_PREV*(1-COEF) \quad \text{formula (3)}$$

$$AVE\_RT\_PREV = AVE\_RT \quad \text{formula (4)}$$

AVE_RT: average response time
AVE_RT_PREV: past average response time
COEF: smoothing coefficient (for example, 0.9)

The time averaging section 171 outputs the average response time obtained by the formula (3) to the hearing characteristic estimate section 175, and updates the past average response time with the formula (4) to store it into the buffer 173. This makes it possible to reduce an influence of a local variation in response times.

Figure 7:
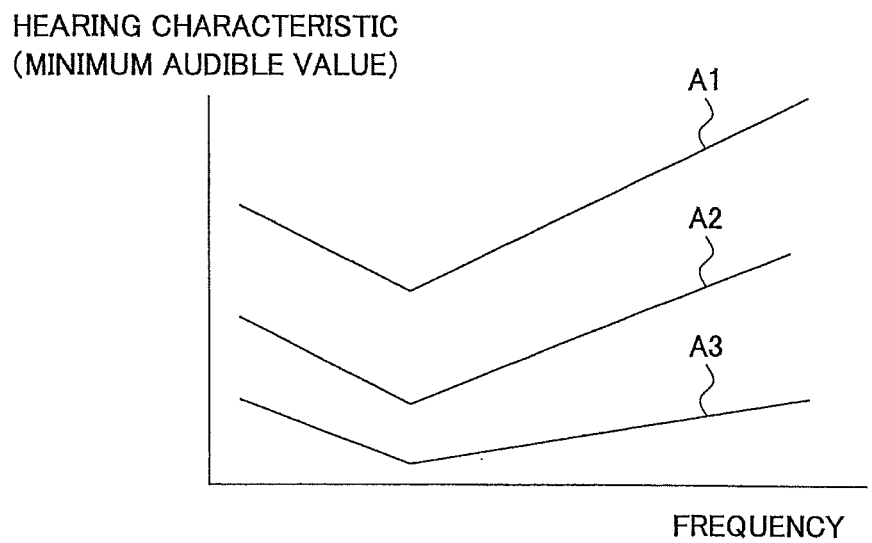
FIG. 7 is a schematic view illustrating a relationship between the average response time and hearing characteristics.

The hearing characteristic estimate section 175 estimates a hearing characteristic (for example, a minimum audible value) from the average response time. FIG. 7 is a schematic view illustrating a relationship between the average response time and hearing characteristics. A hearing characteristic A1 illustrated in FIG. 7 is associated with the average response time of 4 s, a hearing characteristic A2 is associated with the average response time of 2 s, a hearing characteristic A3 is associated with the average response time of 1 s.

The average response time of 4 s represents the average value of 60's, the average response time of 2 s represents the average value of 40's, and the average response time of 1 s represents the average value of 20's. Here, these numerical values of 4, 2, and 1 may be set to appropriate values of the average response times for the ages obtained by an experiment.

The hearing characteristic estimate section 175 identifies a hearing characteristic that is associated with the average response time obtained by the time averaging section 171 using the information illustrated in FIG. 7. The hearing characteristic estimate section 175 outputs the identified hearing characteristic to the voice control section 109.

Here, the hearing estimate section 107 does not estimate hearing if a response time or the average response time is greater than a predetermined threshold value. This makes it possible to exclude an influence of a long pause induced when a conversation breaks off or a topic is changed. The predetermined threshold value may be set, for example, greater than the average response time of the oldest age in an experiment.

Returning to FIG. 2, the voice control section 109 controls the received signal (received sound spectrum) obtained from the time-frequency transform section 101, using compensation quantity obtained from the hearing estimate section 107. For example, the voice control section 109 controls the received signal to take a greater value than the estimated hearing characteristic (for example, a minimum audible value) of the user.

Figure 8:
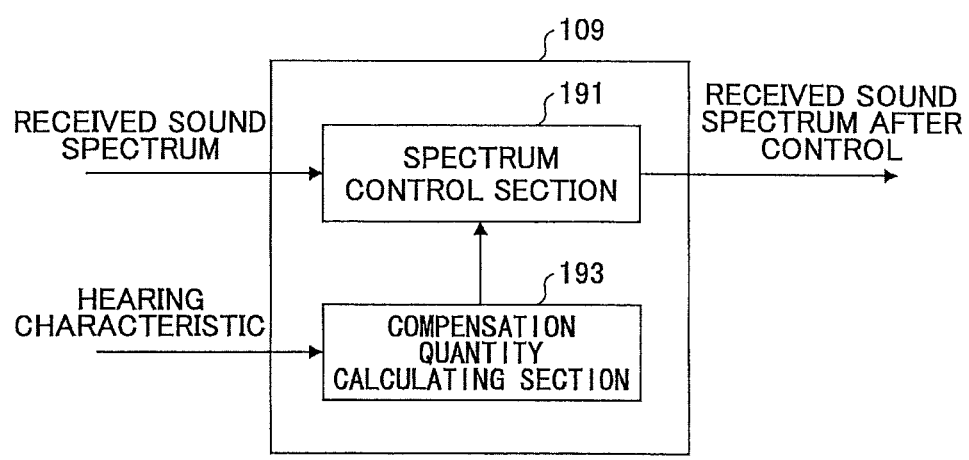
FIG. 8 is a block diagram illustrating an example of a configuration of a voice control section according to the first embodiment.

FIG. 8 is a block diagram illustrating an example of a configuration of the voice control section 109 according to the first embodiment. In an example illustrated in FIG. 8, the voice control section 109 includes a spectrum control section 191 and a compensation quantity calculating section 193.

Figure 9:
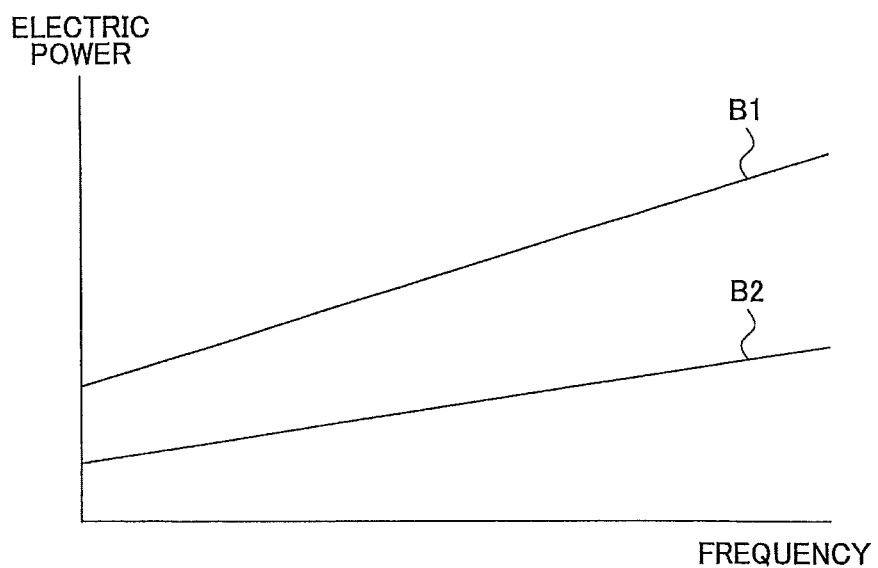
FIG. 9 is a schematic view illustrating calculation of a compensation quantity.

The compensation quantity calculating section 193 obtains a hearing characteristic from the hearing estimate section 107 to calculate compensation quantity in response to the obtained hearing characteristic. The compensation quantity calculating section 193 outputs the calculated compensation quantity to the spectrum control section 191. FIG. 9 is a schematic view illustrating calculation of compensation quantity.

B1 illustrated in FIG. 9 represents hearing reduction quantity. Hearing reduction quantity is quantity obtained by subtracting the minimum audible value of 20's from the estimated minimum audible value of the user. B2 illustrated in FIG. 9 represents the compensation quantity. The compensation quantity may be set to, for example, half of the hearing reduction quantity. The compensation quantity is, for example, enhanced gain.

Various gain calculation methods used for hearing aids or the like can be applied to the compensation quantity. As an example of a gain calculation, there is a gain calculation method using the half gain method described above. As for the gain calculation method, refer to <http://www.okayama.med.or.jp/ishi/bukai/h18kenshukai/05.pdf> (half gain method, POGO method, NAL method), and <http://www.tokyo-hotyouki.co.jp/siryou.htm> (half gain method, Shapiro method, Klingbeil method, Berger method, POGO method).

Figure 10:
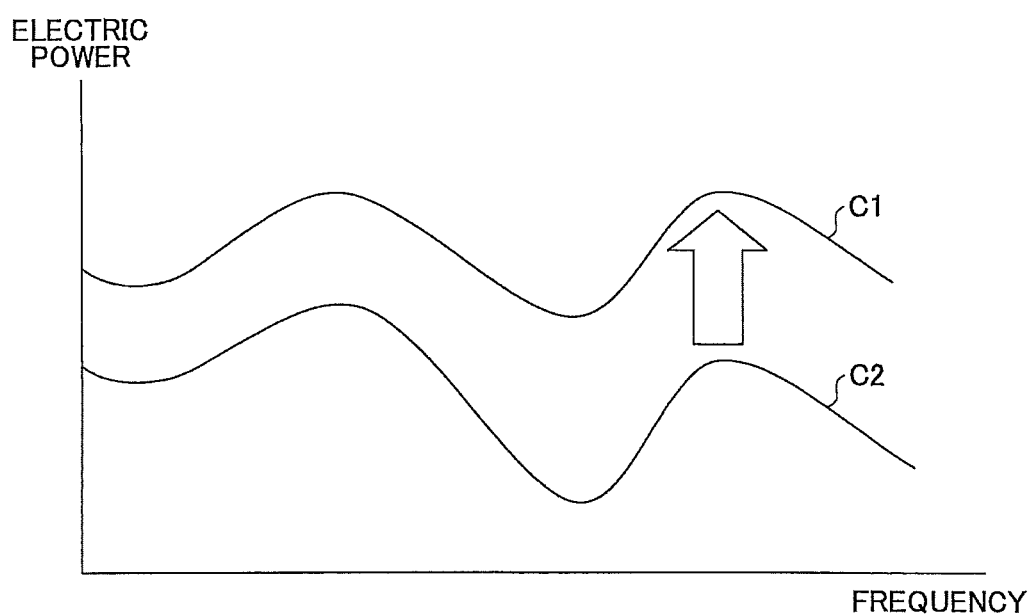
FIG. 10 is a schematic view illustrating an example of spectrum control.

Returning to FIG. 8, the spectrum control section 191 controls the received signal using the compensation quantity obtained from the compensation quantity calculating section 193. For example, the spectrum control section 191 amplifies the compensation quantity (for example, enhanced gain quantity) for each frequency in the received sound spectrum by the following formula (5).

$$F'(j) = \text{gain}(j)*F(j) \quad \text{formula (5)}$$

j: frequency bin (j=1 to 256)
F(j): received sound spectrum
gain(j): compensation quantity FIG. 10 is a schematic view illustrating an example of spectrum control. C2 illustrated in FIG. 10 represents a received sound spectrum before control, and C1 represents a received sound spectrum after control. The spectrum control section 191 amplifies the received sound spectrum C2 with the compensation quantity obtained from the compensation quantity calculating section 193 to control the received sound spectrum C1. The spectrum control section 193 outputs the controlled received sound spectrum to the frequency-time transform section 111.

Returning to FIG. 2, the frequency-time transform section 111 obtains the controlled received sound spectrum from the voice control section 109, to apply a frequency-time transform to the received signal for transforming the received signal into the time domain. The frequency-time transform section 111 transforms the received signal into the time domain, for example, by the following formula (6).

$$x_k = \frac{1}{n}\sum_{k=0}^{n-1} F'(j)e^{\frac{2\pi i}{n}jk}$$ formula (6)

F'(j): received sound spectrum after control
n: FFT analysis length (for example, 256)
j: frequency bin
k: Nyquist frequency A speaker 115 outputs the received signal transformed into the time domain. This makes it possible for a user to hear a processed sound (received sound) in response to the hearing of the user just by making a conversation through a terminal without being aware of terminal operations.

<Operation>

Figure 11:
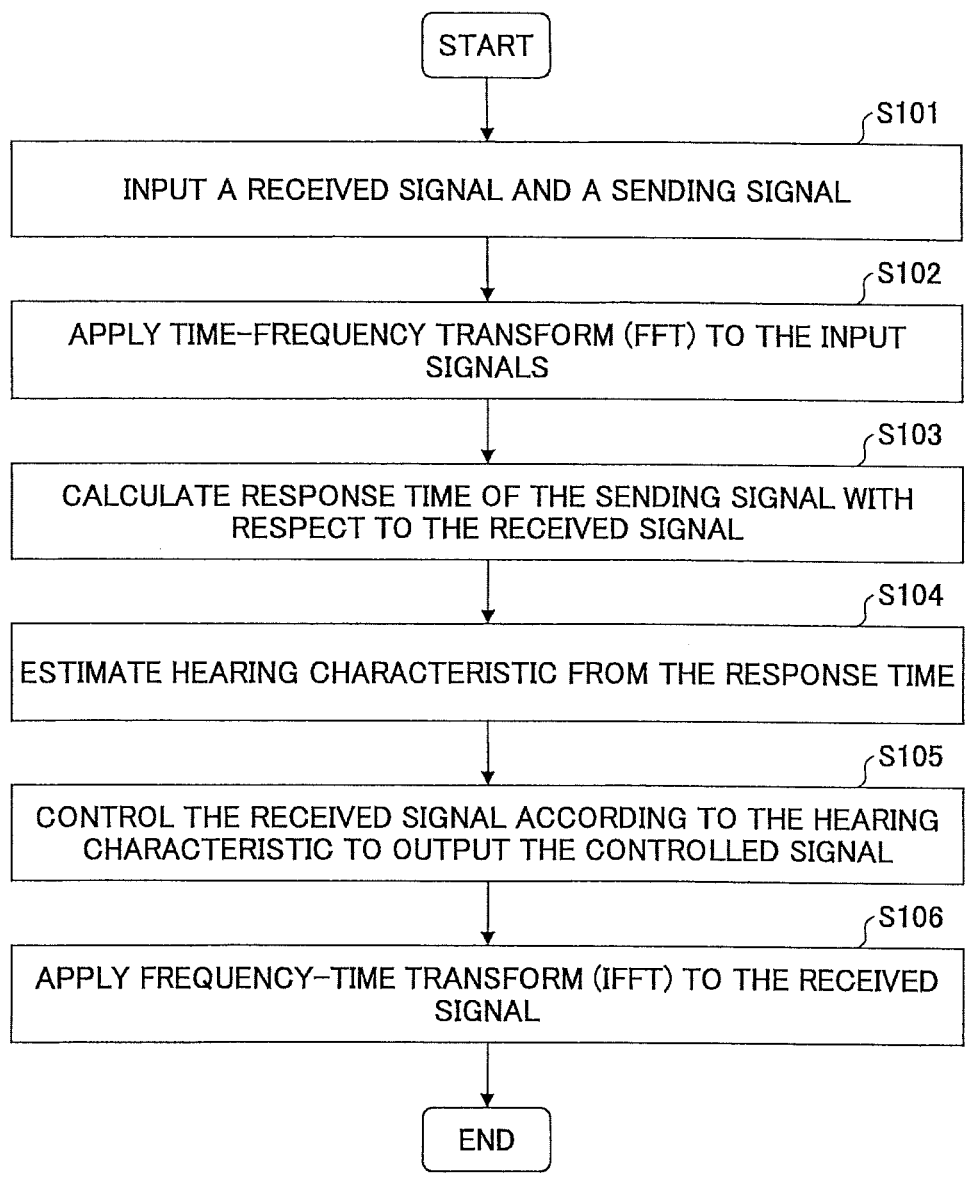
FIG. 11 is a flowchart illustrating an example of voice control according to the first embodiment.

Next, operations of the voice control device 1 will be described according to the first embodiment. FIG. 11 is a flowchart illustrating an example of voice control according to the first embodiment.

At Step S101 illustrated in FIG. 11, the voice control device 1 inputs the received signal and the sending signal.

At Step S102, the time-frequency transform sections 101 and 103 apply a time-frequency transform (FFT) to the input signals, for example, by the formula 1.

At Step S103, the response time calculating section 105 calculates the response time of the sending signal with respect to the received signal. For example, the response time calculating section 105 determines voice segments in the received signal and the sending signal, then calculates a time difference between the ending time of the voice segment in the received signal and the starting time of the voice segment in the sending signal.

At Step S104, the hearing estimate section 107 estimates hearing of the user from the response time. For example, the hearing estimate section 107 holds a hearing characteristic associated with the response time or the average response time (for example, see FIG. 7), and obtains the hearing characteristic associated with the calculated response time or the average response time. The hearing characteristic is, for example, the minimum audible value.

At Step S105, the voice control section 109 controls the received signal with a compensation quantity in response to the estimated hearing characteristic (for example, see FIGS. 9 and 10), to output the controlled signal to the frequency-time transform section 111.

At Step S106, the frequency-time transform section 111 applies a frequency-time transform (IFFT) to the received signal output from the voice control section 109, to transform the received signal into the time domain.

Thus, according to the first embodiment, it is possible to estimate hearing of a user from a response time to control voice in response to the estimated hearing of the user. It is also possible, according to the first embodiment, to remove a local variation of response times by calculating the average response time to estimate hearing of a user.

Also, according to the first embodiment, it is possible to avoid an inappropriate calculation of a response time by not calculating a response time if a received signal and a sending signal overlap along the timeline. Also, according to the first embodiment, it is possible to estimate hearing based on an appropriate response time by not executing a hearing estimation if the response time is too long.

Second Embodiment

Next, a voice control device 2 will be described according to the second embodiment. In, the second embodiment, time length is calculated for a voice segment in a received signal and a voice segment in a sending signal, to take the calculated time length into account for calculation of a response time.

<Configuration>

Figure 12:
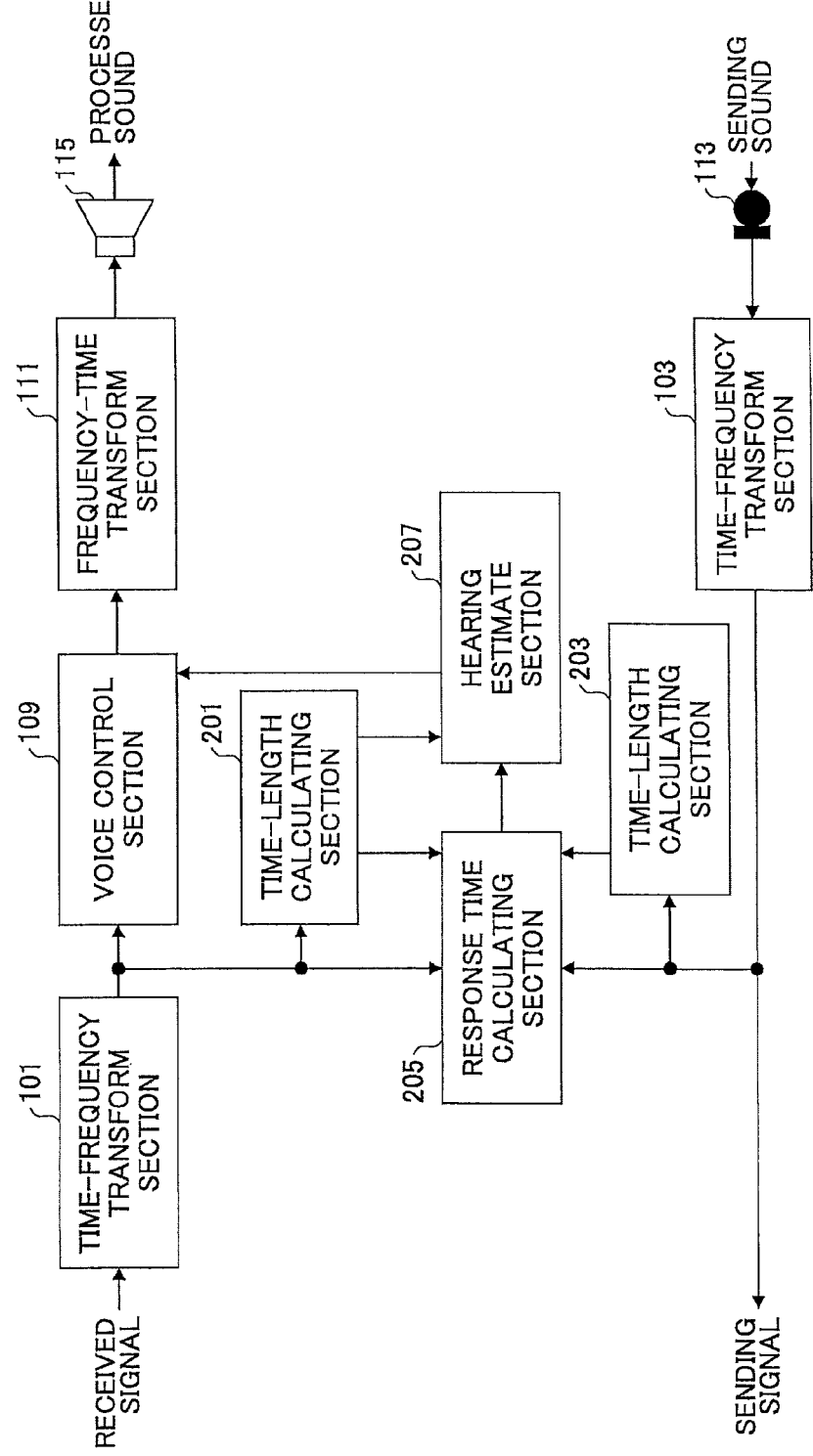
FIG. 12 is a block diagram illustrating an example of a configuration of a voice control device according to a second embodiment.

FIG. 12 is a block diagram illustrating an example of a configuration of a voice control device 2 according to the second embodiment. The voice control device 2 illustrated in FIG. 12 includes time-frequency transform sections 101 and 103, time-length calculating sections 201 and 203, a response time calculating section 205, a hearing estimate section 207, a voice control section 109, and a frequency-time transform section 111.

In the configuration illustrated in FIG. 12, the same numeral codes are given to the same elements as in the configuration illustrated in FIG. 2, whose explanation is omitted. The time-length calculating section 201 illustrated in FIG. 12 calculates a time length of a voice segment in a received signal. The time-length calculating section 201, similar to the first voice determining section 151 described above, determines a voice segment in a received signal to calculate the time length of the voice segment.

Figure 13:
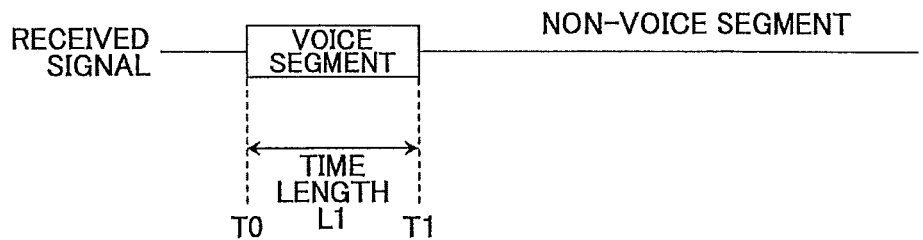
FIG. 13 is a schematic view illustrating calculation of a time length.

FIG. 13 is a schematic view illustrating calculation of a time length. As illustrated in FIG. 13, the time-length calculating section 201 calculates a time length L1 from the starting time T0 to the ending time T1 of a voice segment in a received signal. The time-length calculating section 201 outputs the calculated time length L1 to the response time calculating section 205 and the hearing estimate section 207.

The time-length calculating section 203 calculates the time length of a voice segment in a sending signal. The time-length calculating section 203, similar to the second voice determining section 153 described above, determines a voice segment in a sending signal to calculate the time length of the voice segment. The time-length calculating section 203 outputs the calculated time length L2 of the sending voice to the response time calculating section 205.

Figure 14:
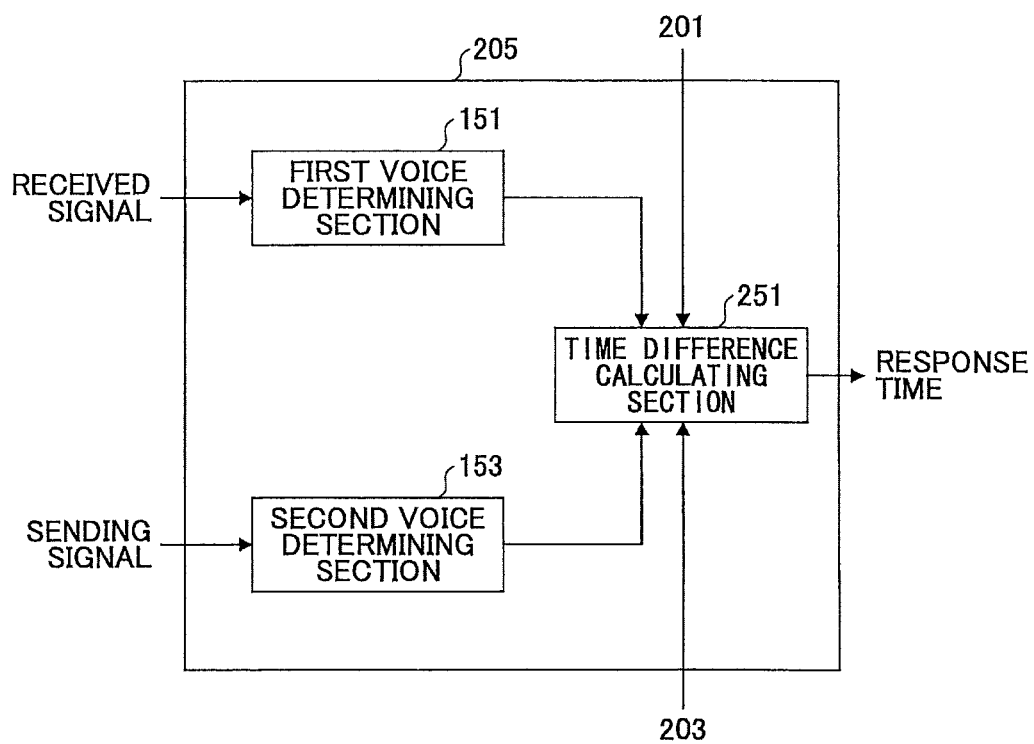
FIG. 14 is a block diagram illustrating an example of a configuration of a response time calculating section according to the second embodiment.

The response time calculating section 205 determines whether to calculate a response time based on the time length of received voice and/or the time length of the sending signal. FIG. 14 is a block diagram illustrating an example of a configuration of the response time calculating section 205 according to the second embodiment.

The response time calculating section 205 illustrated in FIG. 14 includes a first voice determining section 151, a second voice determining section 153, and a time difference calculating section 251. In the configuration illustrated in FIG. 14, the same numeral codes are given to the same elements as in the configuration illustrated in FIG. 3, whose explanation is omitted.

The time difference calculating section 251 obtains the time length L1 of the received voice from the time-length calculating section 201, and the time length L2 of the sending voice from the time-length calculating section 203. The time difference calculating section 251 obtains the ending time T1 of the received voice from the first voice determining section 151, and the starting time T2 of the sending voice from the second voice determining section 153.

The time difference calculating section 251 does not calculate a response time if the time length L1 of the received voice is shorter than a predetermined threshold value, hence the received voice cannot be viewed as a conversation. The predetermined threshold value may be set to an appropriate value by an experiment that measures lengths of received voices in conversations. This makes it possible to exclude a calculation of a response time based on a word asking for repetition in received voices.

The time difference calculating section 251 does not calculate a response time if the time length L1 of a sending voice is shorter than a predetermined threshold value, hence the sending voice cannot be viewed as a conversation. The predetermined threshold value may be set to an appropriate value by an experiment that measures lengths of sending voices in conversations. This makes it possible to exclude a calculation of a response time based on a word asking for repetition or the like in sending voices. Calculation of a response time is executed in the same way as in the first embodiment.

Here, functions of the time-length calculating section 201 and 203 may be implemented in the time difference calculating section 251, because the time difference calculating section 251 can recognize a voice segment in a received signal and a voice segment in a sending signal. Also, the time difference calculating section 251 may determine whether to calculate a response time only using either of the time length of a received voice or the time length of a sending signal.

Returning to FIG. 12, the hearing estimate section 207 estimates hearing of a user based on the response time calculated by the response time calculating section 205. Here, the hearing estimate section 207 executes a different procedure from the one in the first embodiment when obtaining the average response time, which will be described in the following.

Figure 15:
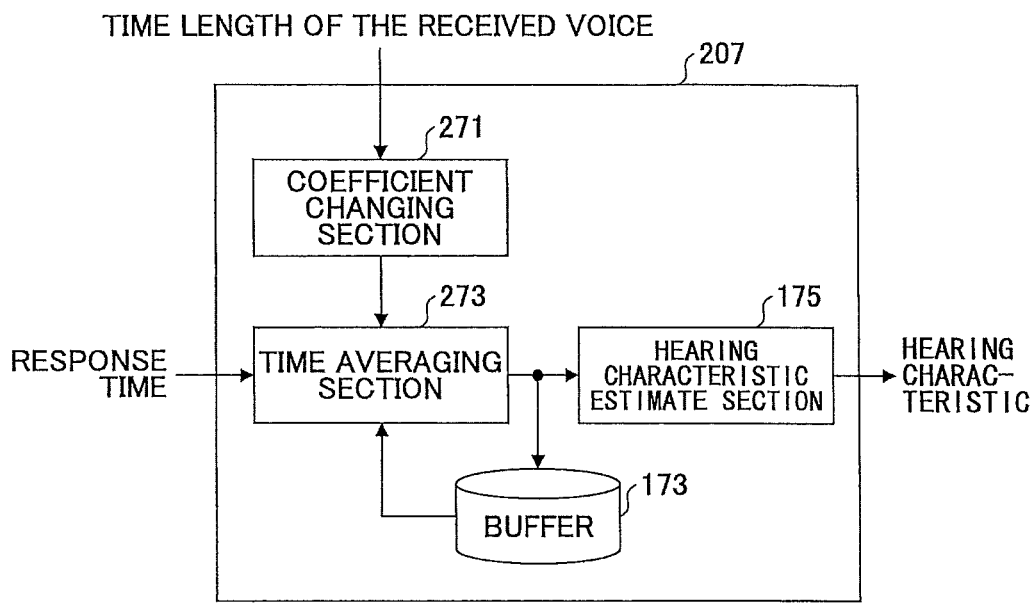
FIG. 15 is a block diagram illustrating an example of a configuration of a hearing estimate section of estimating hearing from the average value of response times according to the second embodiment.

FIG. 15 is a block diagram illustrating an example of a configuration of the hearing estimate section 207 if estimating hearing from the average value of response times according to the second embodiment. The hearing estimate section 207 illustrated in FIG. 15 includes a coefficient changing section 271, a time averaging section 273, a buffer 173, and a hearing characteristic estimate section 175. In the configuration illustrated in FIG. 15, the same numeral codes are given to the same elements as in the configuration illustrated in FIG. 6, whose explanation is omitted.

The coefficient changing section 271 updates (changes) a smoothing coefficient used for the time-average of response times in response to the time length of a received voice. The coefficient changing section 271, for example, increases the smoothing coefficient if the time length of a received voice is long, but decreases the smoothing coefficient if the time length of a received voice is short.

This is to make a contribution degree of the response time great for a long received voice. When getting older, one cannot remember a long voice content, so that the average value of response times for a long voice may represent a change in response times for generations.

Figure 16:
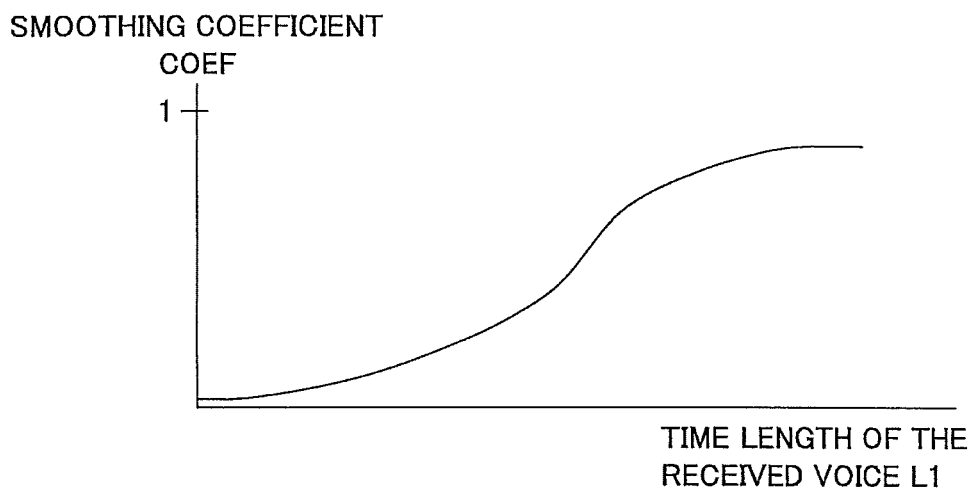
FIG. 16 is a schematic view illustrating a relationship between time length of a received voice and a smoothing coefficient.

FIG. 16 is a schematic view illustrating a relationship between the time length of a received voice and the smoothing coefficient. The coefficient changing section 271 holds, for example, information illustrated in FIG. 16 to obtain a smoothing coefficient COEF corresponding to a time length L1 of a received voice. As illustrated in FIG. 16, the greater the time length L1 is, the greater the smoothing coefficient COEF becomes. The coefficient changing section 271 outputs the obtained smoothing coefficient to the time averaging section 273.

Returning to FIG. 15, the time averaging section 273 calculates the average value of response times (average response time) using the smoothing coefficient obtained from the coefficient changing section 271. The average response time can be obtained with the formula (3) described above. The time averaging section 273 outputs the obtained average response time to the hearing characteristic estimate section 175, and stores the obtained average response time into a buffer 173 as the past average response time. Here, the time length L1 of the received signal may be used only for obtaining the smoothing coefficient. The rest of the processing is the same as in the first embodiment.

<Operation>

Figure 17:
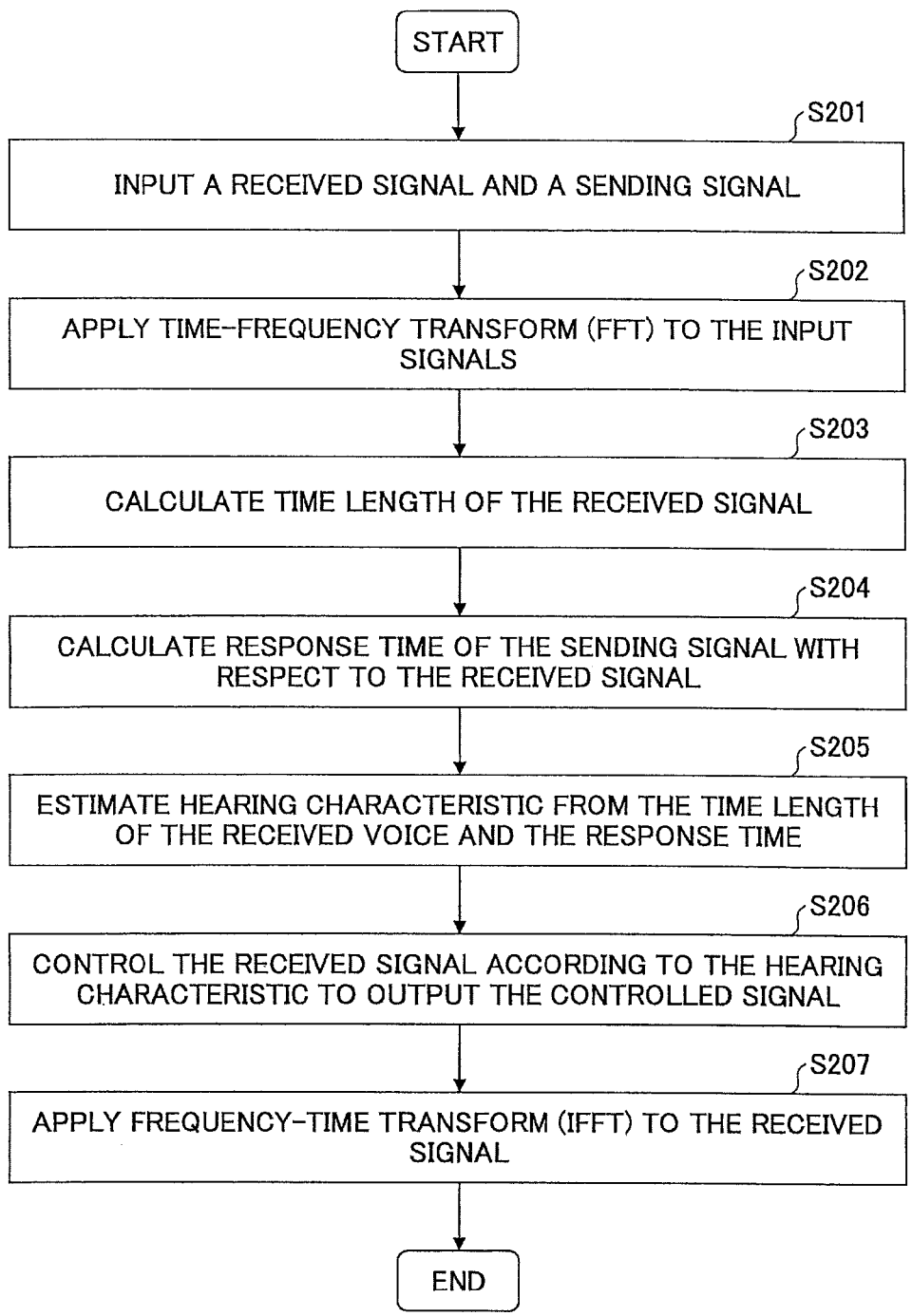
FIG. 17 is a flowchart illustrating an example of a voice control procedure according to the second embodiment.

Next, operations of the voice control device 2 will be described according to the second embodiment. FIG. 17 is a flowchart illustrating an example of a voice control procedure according to the second embodiment. The flow illustrated in FIG. 17 is a processing flow for calculating the average response time using the smoothing coefficient corresponding to the time length of a received voice.

Steps S201, S202, S206, and S207 illustrated in FIG. 17 are the same as the Steps S101, S102, S105, and S106 illustrated in FIG. 1, whose explanation is omitted.

At Step S203, the time-length calculating section 201 calculates the time length of a voice segment in the received signal.

At Step S204, the response time calculating section 205 calculates the response time of the sending signal to the received signal. At this moment, if the time length of the received voice and/or the time length of the sending signal is shorter than a threshold value, the response time may not be calculated.

At Step S205, the hearing estimate section 207 calculates the average response time using the smoothing coefficient corresponding to the time length of the received voice. The hearing estimate section 207 estimates a hearing characteristic of the user based on the calculated average response time. The rest of the processing is the same as in the first embodiment.

Thus, according to the second embodiment, it is possible to calculate the response time in an appropriate conversation by determining whether to calculate a response time based on the time length of a voice segment in a received signal and/or a voice segment in a sending signal. Also, according to the second embodiment, it is possible to make the difference of response times among generations more distinguished by calculating the average response time having the weight of the response time greater if the time length of a voice segment in a received signal is longer.

Third Embodiment

Next, a voice control device will be described according to the third embodiment. A voice control device in the third embodiment calculates an articulation rate, then calculates a response time if the received signal is articulated.

<Configuration>

Figure 18:
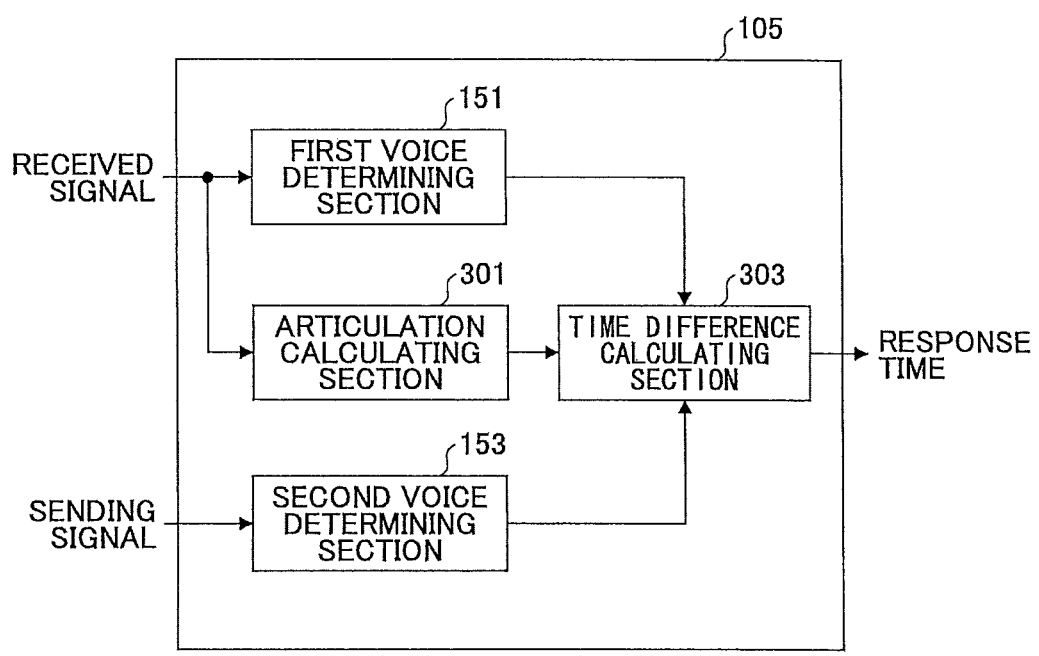
FIG. 18 is a block diagram illustrating an example of a configuration of a response time calculating section according to a third embodiment.

In the third embodiment, the configuration of the voice control device is the same as in FIG. 2. In the third embodiment, the response time calculating section 105 has a different configuration from the one in the first embodiment, which will be described in the following. FIG. 18 is a block diagram illustrating an example of a configuration of the response time calculating section 105 according to the third embodiment.

The response time calculating section 105 illustrated in FIG. 18 includes a first voice determining section 151, a second voice determining section 153, an articulation calculating section 301, and a time difference calculating section 303. In the configuration illustrated in FIG. 18, the same numeral codes are given to the same elements as in the configuration illustrated in FIG. 3, whose explanation is omitted.

The articulation calculating section 301 calculates an arbitration rate of a received signal. The articulation calculating section 301 can determine an articulation of a voice, for example, with the slope of the power spectrum of a received signal. The articulation rate is low if the slope of the power spectrum is small, whereas the articulation rate is high if the slope of the power spectrum is great.

The articulation calculating section 301 calculates a low range (0 to 2 kHz) average power PW_l, and a high range (2 to 4 kHz) average power PW_h. The articulation calculating section 301 calculates the articulation rate, for example, with the following formula (7).

$$CL=PW\_h-PW\_l \quad \text{formula (7)}$$

CL: articulation rate

The articulation calculating section 301 outputs the calculated articulation rate CL to the time difference calculating section 303.

The time difference calculating section 303 calculates the response time if the absolute value of the obtained articulation rate is greater than a threshold value, hence the received signal is articulated. The threshold value may be set to, for example, 3 dB (decibel). The time difference calculating section 303 does not calculate the response time if the obtained articulation rate CL is lower than the threshold value. This is because an influence of a received voice with a low articulation rate is excluded, which makes it difficult to hear regardless of hearing. The time difference calculating section 303 outputs the calculated response time to the hearing estimate section 107. The rest of the processing is the same as in the first embodiment.

<Operation>

Figure 19:
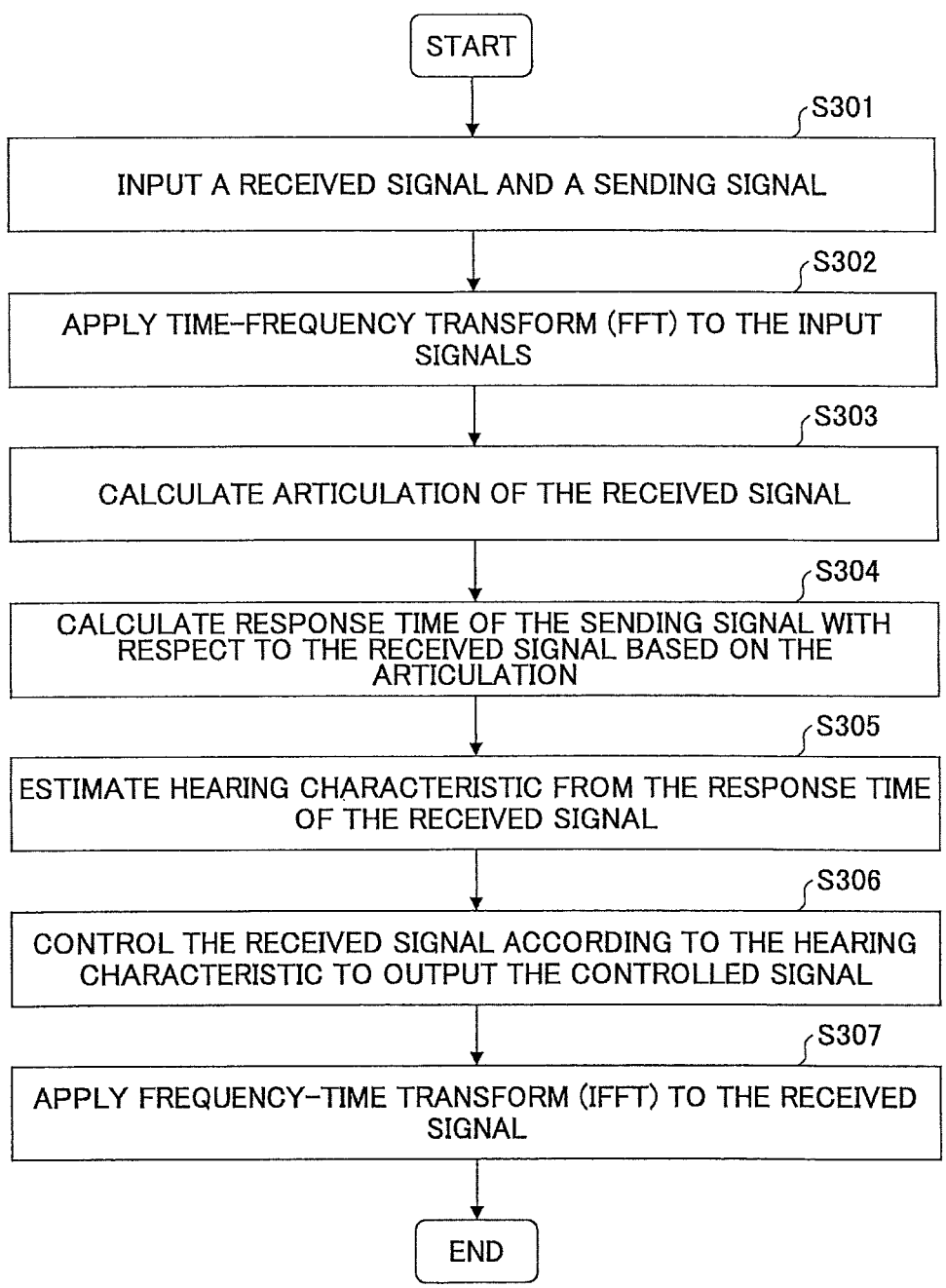
FIG. 19 is a flowchart illustrating an example of a voice control procedure according to the third embodiment.

Next, operations of the voice control device will be described according to the third embodiment. FIG. 19 is a flowchart illustrating an example of a voice control procedure according to the third embodiment. Steps S301, S302, S305 to S307 illustrated in FIG. 19 are the same as Steps S101, S102, S104 to S106 illustrated in FIG. 11, respectively, whose explanation is omitted.

At Step S303, the articulation calculating section 301 calculates the articulation rate of the received signal. The articulation calculating section 301 determining the articulation rate of the voice, for example, with the slope of the power spectrum of the received signal.

At Step S304, the time difference calculating section 303 calculates the response time if the calculated articulation rate is greater than a predetermined threshold value. The rest of the processing is the same as in the first embodiment.

Thus, according to the third embodiment, it is possible to estimate hearing with a high precision because hearing is estimated by calculating an articulation rate of a received signal, then calculating the response time if the received signal is sufficiently articulated.

Fourth Embodiment

Next, a voice control device 4 will be described according to the fourth embodiment. In the fourth embodiment, an effect of voice control is evaluated with a time change in response times to feedback the effect to voice control.

<Configuration>

Figure 20:
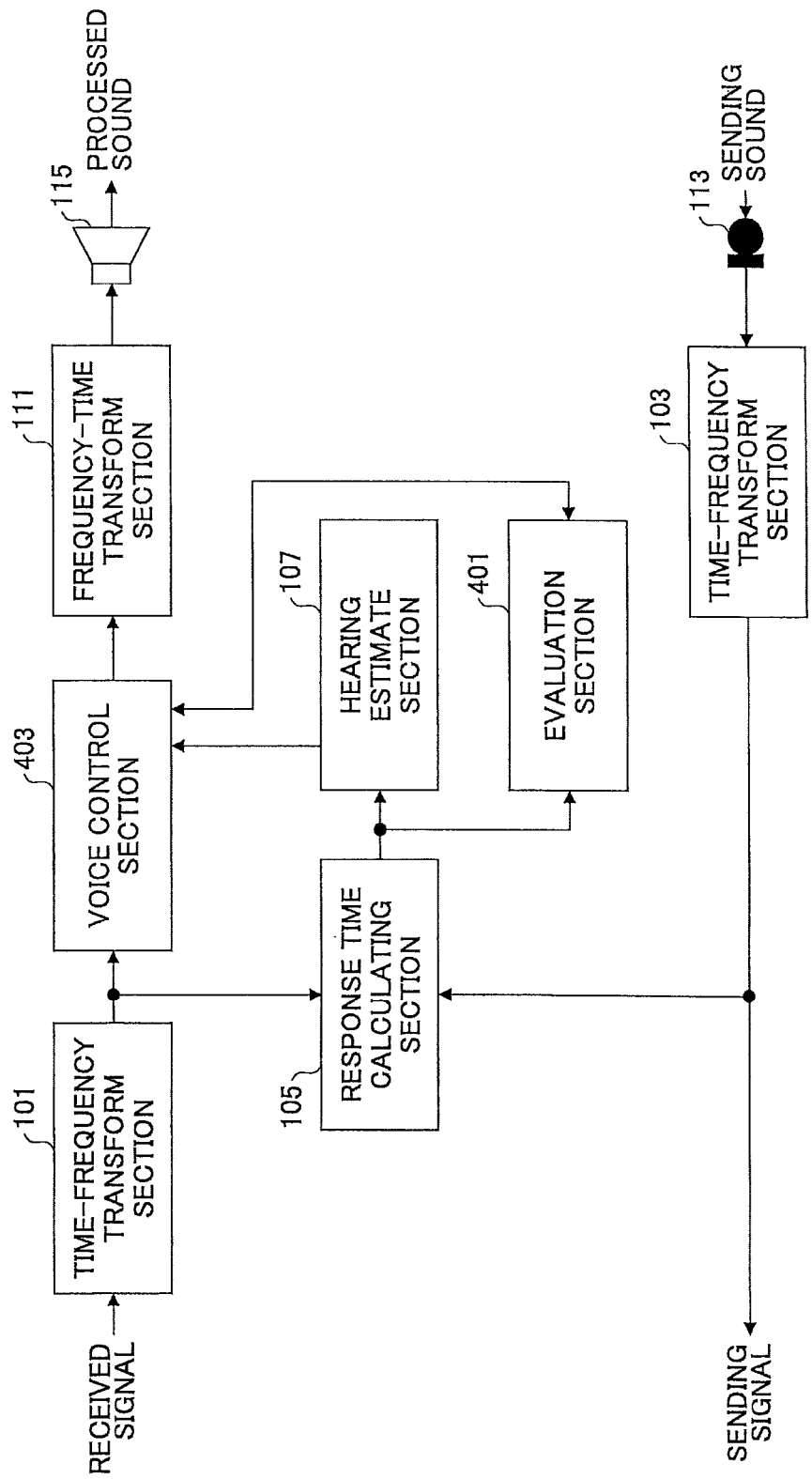
FIG. 20 is a block diagram illustrating an example of a configuration of a voice control device according to a fourth embodiment.

FIG. 20 is a block diagram illustrating an example of a configuration of the voice control device 4 according to the fourth embodiment. The voice control device 4 illustrated in FIG. 20 includes time-frequency transform sections 101 and 103, a response time calculating section 105, a hearing estimate section 107, a frequency-time transform section 111, an evaluation section 401, and a voice control section 403. In the configuration illustrated in FIG. 20, the same numeral codes are given to the same elements as in the configuration illustrated in FIG. 2, whose explanation is omitted.

The evaluation section 401 generates control signals for adjusting compensation quantity for a received signal based on a response time obtained from the response time calculating section 105 and compensation quantity obtained from the voice control section 403.

Figure 21:
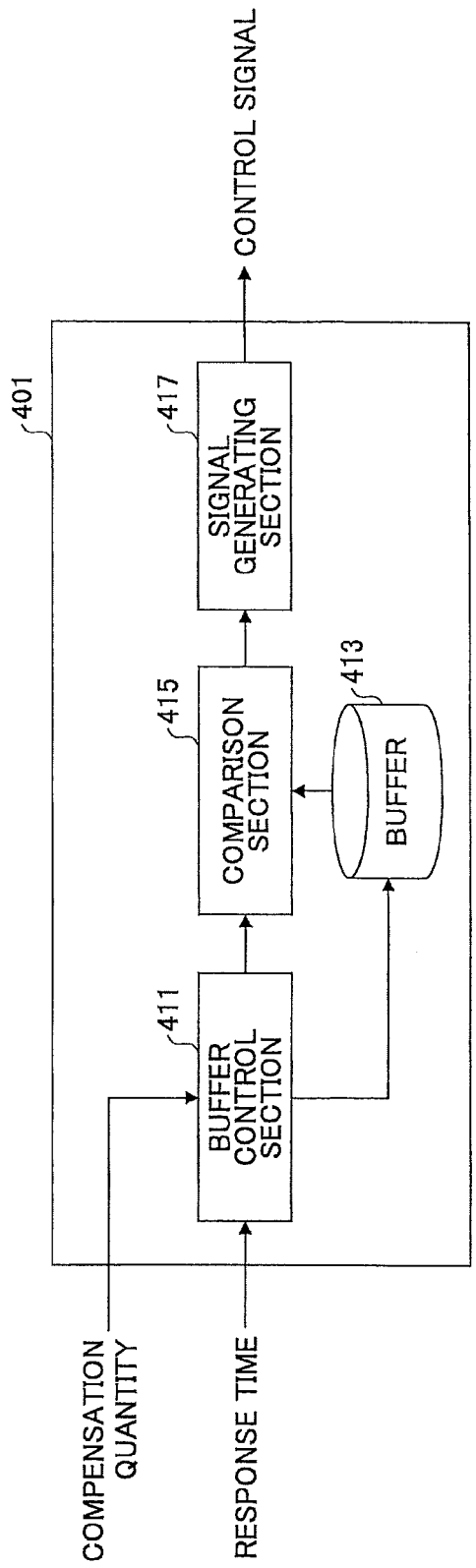
FIG. 21 is a block diagram illustrating an example of a configuration of an evaluation section according to the fourth embodiment.

FIG. 21 is a block diagram illustrating an example of a configuration of the evaluation section 401 according to the fourth embodiment. The evaluation section 401 illustrated in FIG. 21 includes a buffer control section 411, a buffer 413, a comparison section 415, and a signal generating section 417.

The buffer control section 411 obtains a response time from the response time calculating section 105, and obtains compensation quantity of the received signal from the voice control section 403. The buffer control section 411 stores the response time before voice control RT_a into the buffer 413, and outputs the response time after voice control RT_b to the comparison section 415.

The buffer 413 stores the response time before voice control RT_a by the voice control section 403.

The comparison section 415 compares the response time before control RT_a read out from the buffer 413, and the response time after control RT_b obtained from the buffer control section 411, to output a comparison result to the signal generating section 417.

The signal generating section 417 generates control signals for controlling the received signal, based on the comparison result obtained from the comparison section 415. The signal generating section 417 outputs the generated control signals to the voice control section 403.

The signal generating section 417 generates, for example, the following control signals S0 to S2.

S0: control signal for setting gain back to that before control
S1: control signal for enhancing gain
S2: control signal for weakening gain The signal generating section 417 generates the control signal S1 for enhancing gain if the response time is reduced. This is because it can be considered that a gain change has had an effect if the response time is reduced. The signal generating section 417 generates the control signal for enhancing the gain until the response time is not reduced anymore.

The signal generating section 417 generates the control signals S0 and S2 for weakening gain by setting the gain back to the one before control if the response time is not reduced. This is because it can be considered that a gain change has had no effects if the response time is not reduced. After setting back the gain to the one before change, the signal generating section 417 weakens the gain until the response time is not reduced anymore. This is because the gain in the first place might have been enhanced too much for a user to hear the sound properly.

Returning to FIG. 20, the voice control section 403 adjusts compensation quantity based on the control signals obtained from the evaluation section 401, then controls the received signal using the adjusted compensation quantity. The compensation quantity is, for example, gain.

Figure 22:
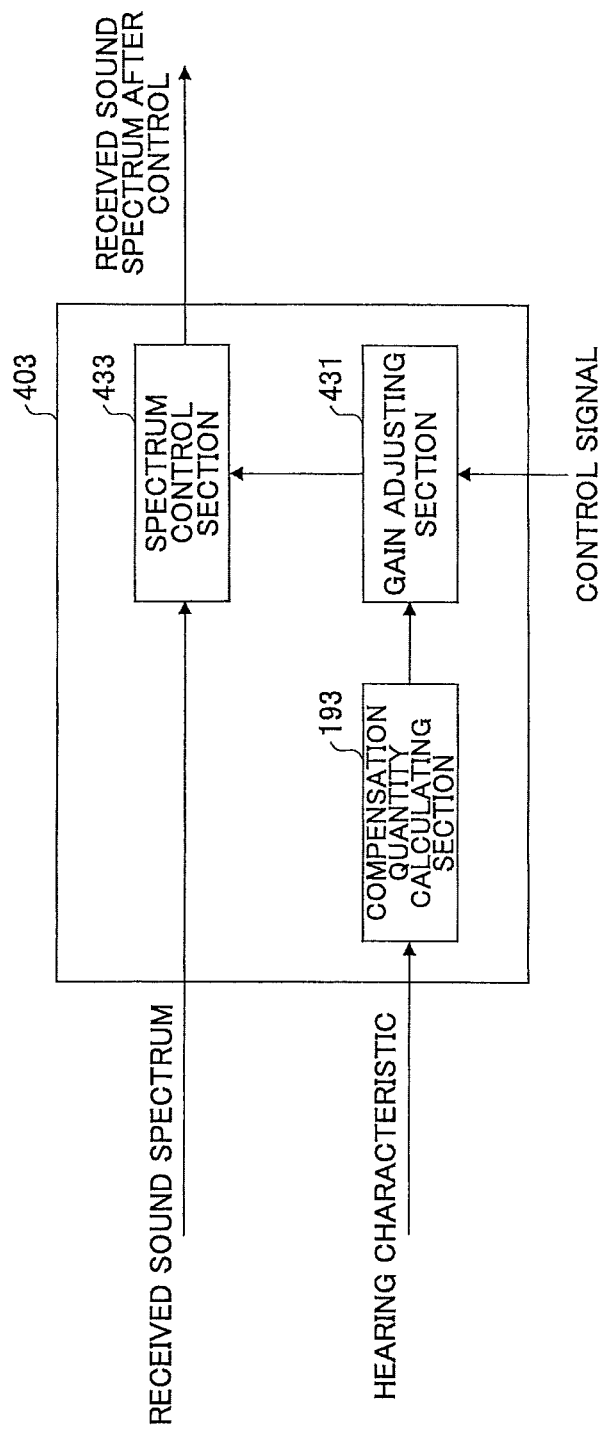
FIG. 22 is a block diagram illustrating an example of a configuration of a voice control section according to the fourth embodiment.

FIG. 22 is a block diagram illustrating an example of a configuration of the voice control section 403 according to the fourth embodiment. The voice control section 403 illustrated in FIG. 22 includes a compensation quantity calculating section 193, a gain adjusting section 431, and a spectrum control section 433. In the configuration illustrated in FIG. 22, the same numeral codes are given to the same elements as in the configuration illustrated in FIG. 8, whose explanation is omitted.

The gain adjusting section 431 adjusts the compensation quantity, which is calculated from a hearing characteristic (for example, a minimum audible value), based on the control signals. The gain adjusting section 431 adjusts the compensation quantity (gain) by the following formula (8).

$$\text{gain}'(j) = \text{gain}(j) + D \quad \text{formula (8)}$$

gain(j): compensation quantity (enhanced gain)
j: frequency bin (j=1 to 256)
D: gain adjustment quantity
gain'(j): compensation quantity after adjustment The gain adjusting section 431 changes the adjustment quantity D by the control signals. If receiving the control signal S0, the gain adjusting section 431 sets the adjustment quantity D so that it is subtracted just by the quantity compensated at the previous time. This makes it possible to set the gain back to the one before control.

If receiving the control signal S1, the gain adjusting section 431 sets the adjustment quantity D to a predetermined value so that the gain is enhanced even further.

If receiving the control signal S2, the gain adjusting section 431 sets the adjustment quantity D to a predetermined minus value so that the gain is weakened.

The gain adjusting section 431 outputs the adjusted compensation quantity gain'(j) to the spectrum control section 433.

The spectrum control section 433 controls the received sound spectrum using the compensation quantity obtained from the gain adjusting section 431. The control method is the same as in the first embodiment.

<Operation>

Figure 23:
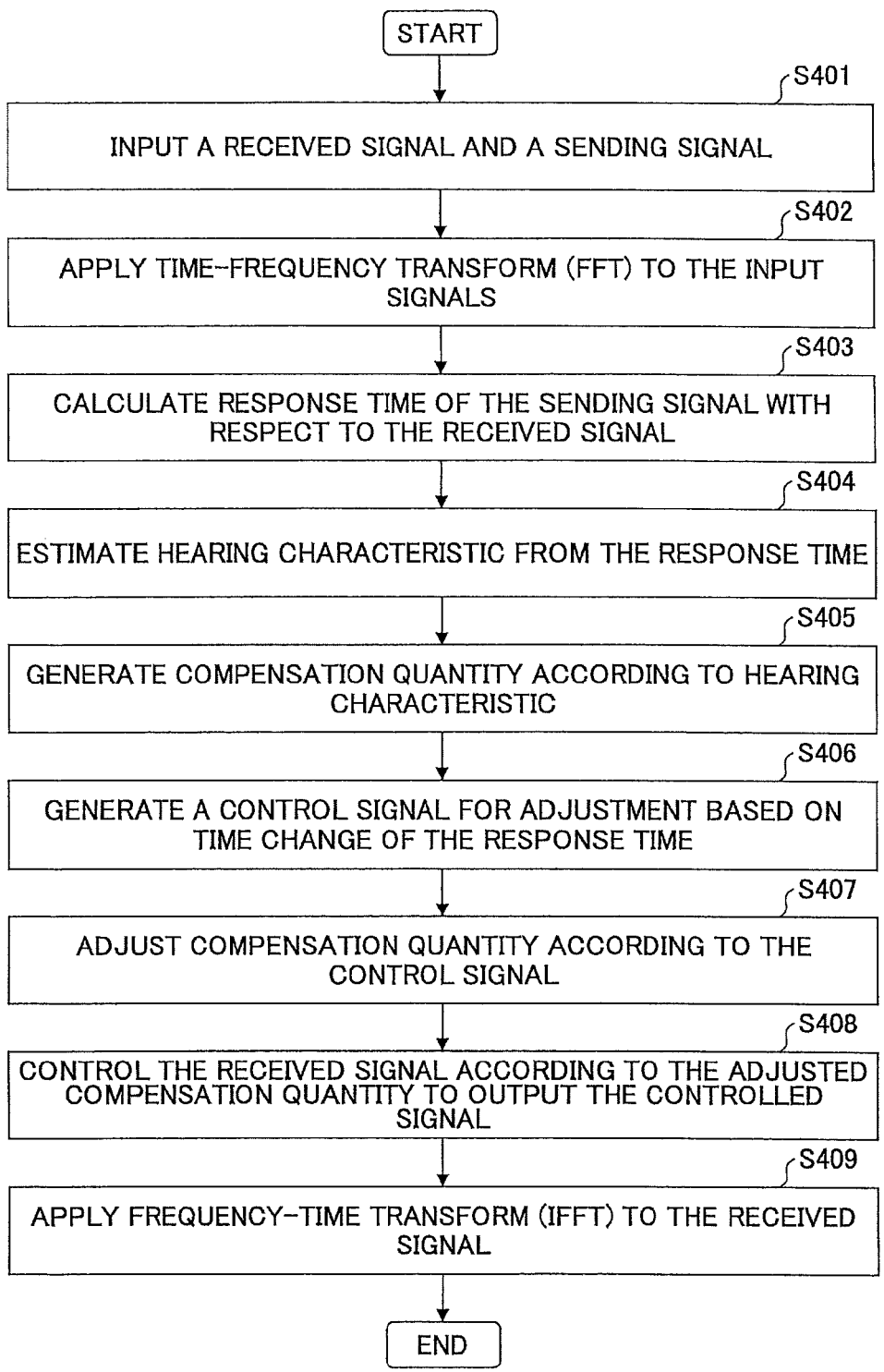
FIG. 23 is a flowchart illustrating an example of a voice control procedure according to the fourth embodiment.

Next, operations of the voice control device will be described according to the fourth embodiment. FIG. 23 is a flowchart illustrating an example of a voice control procedure according to the fourth embodiment. Steps S401 to S404, and S409 illustrated in FIG. 23 are the same as Steps S101 to S104, S106 illustrated in FIG. 11, respectively, whose explanation is omitted.

At Step S405, the compensation quantity calculating section 193 calculates a compensation quantity in response to an estimated hearing characteristic. The hearing characteristic is, for example, the minimum audible value, and the compensation quantity is, for example, gain.

At Step S406, the signal generating section 417 generates control signals for adjusting the compensation quantity based on the time change in the response times.

At Step S407, the gain adjusting section 431 adjusts the compensation quantity in response to the control signals as described above.

At Step S408, the spectrum control section 433 controls received signal (received sound spectrum) in response to the adjusted compensation quantity, to output the control received signal to the frequency-time transform section 111. The rest of the processing is the same as in the first embodiment.

Figure 24:
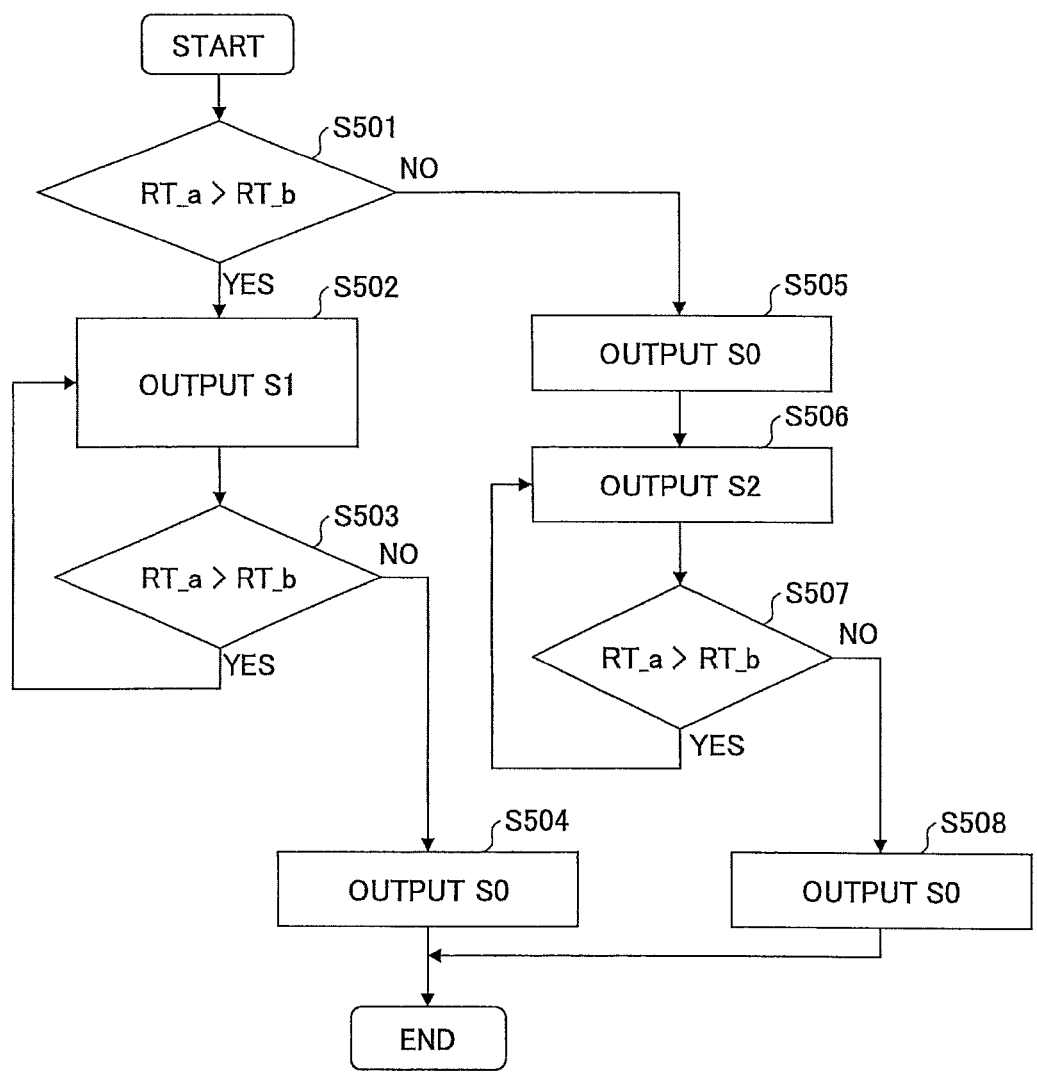
FIG. 24 is a flowchart illustrating an example of a procedure for control signal generation.

Next, a procedure for control signal generation will be described according to the fourth embodiment. FIG. 24 is a flowchart illustrating an example of a procedure for control signal generation. At Step S501 illustrated in FIG. 24, the comparison section 415 determines whether the response time before control RT_a is greater than the response time after control RT_b. If RT_a>RT_b (Step S501-YES), Step S502 is taken, if not RT_a>RT_b (Step S501-NO), Step S505 is taken.

At Step S502, the signal generating section 417 outputs the control signal S1 to the voice control section 403.

At Step S503, the comparison section 415 determines whether the updated RT_a is greater than the updated RT_b. The updated RT_a is RT_b before Step S502 has been processed, and the updated RT_b is the response time calculated after Step S502 has been processed.

If RT_a>RT_b (Step S503-YES), Step S502 is executed again for enhancing the gain, if not RT_a>RT_b (Step S503-NO), Step S504 is taken.

At Step S504, the signal generating section 417 outputs the control signal S0 to the voice control section 403. This makes the compensation quantity be set to an optimal value.

At Step S505, the signal generating section 417 outputs a control signal S0 to the voice control section 403. Step S505 is a step for setting back the gain before control because no effects are obtained with gain enhancement.

At Step S506, the signal generating section 417 outputs the control signal S1 to the voice control section 403. This makes it possible to weaken the compensation quantity.

At Step S507, the comparison section 415 determines whether the updated RT_a is greater than the updated RT_b. The updated RT_a is RT_b before Step S506 has been processed, and the updated RT_b is the response time calculated after Step S506 has been processed.

If RT_a>RT_b (Step S507-YES), Step S506 is executed again for weakening the gain, if not RT_a>RT_b (Step S507-NO), Step S508 is taken.

At Step S508, the signal generating section 417 outputs the control signal S0 to the voice control section 403. This makes the compensation quantity be set to an optimal value.

Thus, according to the fourth embodiment, it is possible to evaluate an effect of voice control with the time change in response times to feedback the effect to the voice control.

Modified Example

Next, a portable terminal device will be described according to a modified example. In the modified example, the example will be described in which the voice control device according to the embodiments is implemented in a portable terminal device.

Figure 25:
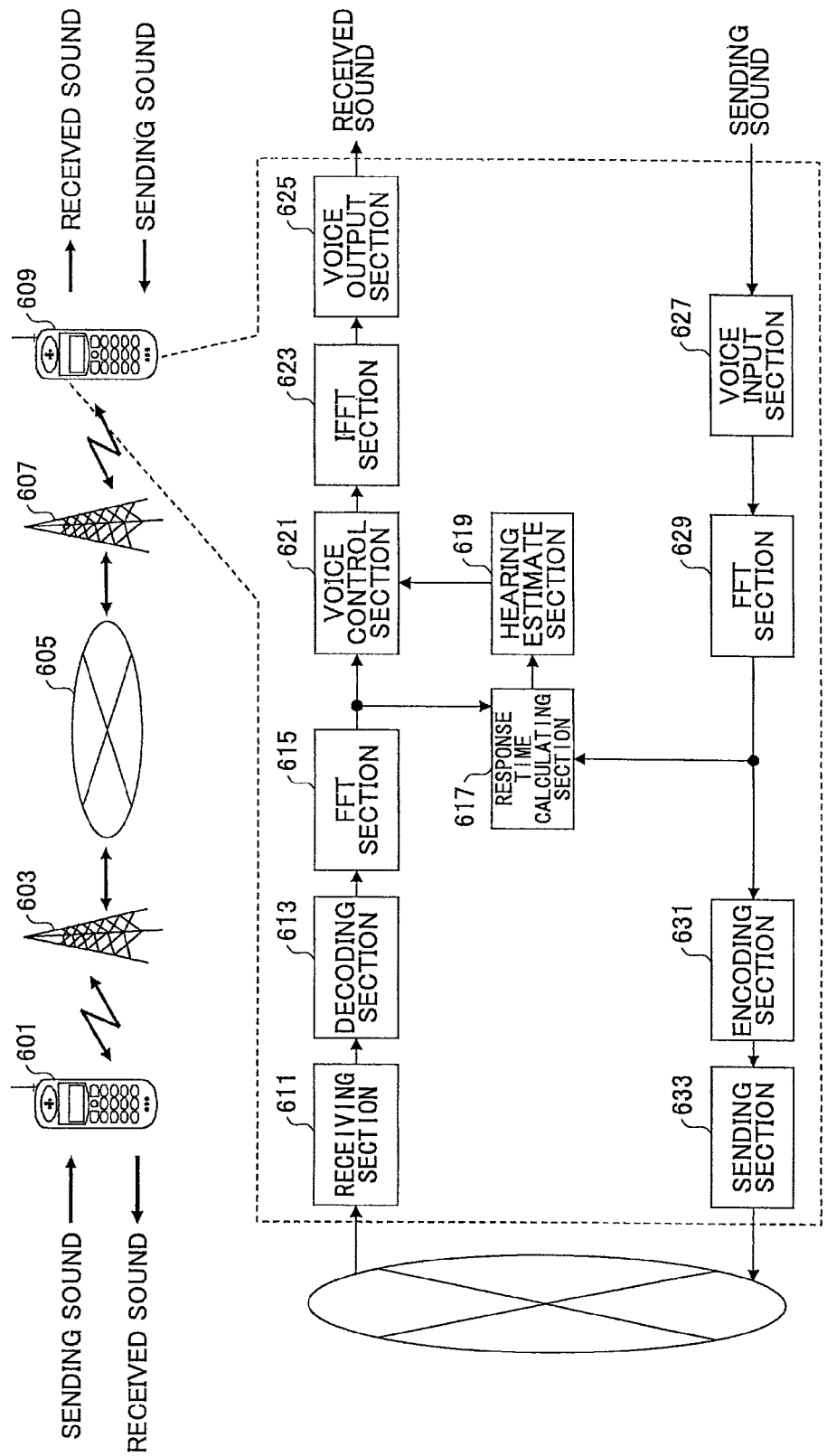
FIG. 25 is a schematic view illustrating a portable terminal device according to a modified example.

FIG. 25 is a schematic view illustrating the portable terminal device according to the modified example. A portable terminal device 609 illustrated in FIG. 25 sends an encoded sending signal to a base station 607, and receives an encoded received signal from the base station 607.

A portable terminal device 601 is a device in the counterpart side, with which a voice signal is encoded to be sent as a received signal received by the portable terminal device 609 via a base station 603, a network 605, and a base station 607.

The portable terminal device 609 illustrated in FIG. 25 includes a receiving section 611, a decoding section 613, an FFT section 615, a response time calculating section 617, a hearing estimate section 619, a voice control section 621, an IFFT section 623, and a voice output section 625.

Also, the portable terminal device 609 includes a voice input section 627, an FFT section 629, an encoding section 631, and a sending section 633.

The voice input section 627 is implemented with a microphone 113 and an A/D converter, to apply an analog-digital conversion to a sending sound output by the microphone 113. The converted signal (sending signal) is output to the FFT section 629.

The FFT section 629 applies a time-frequency transform to the sending signal to generate a sending sound spectrum, which is output to the response time calculating section 617 and the encoding section 631.

The encoding section 631 generates an encoded signal using a general voice encoding technology on the portable terminal device. The sending section 633 sends the encoded signal encoded by the encoding section 631 to the base station 607.

The receiving section 611 receives the encoded signal from the base station 607. The decoding section 613 decodes the encoded signal, which is converted to a voice signal (received signal).

The FFT section 615 applies a time-frequency transform to the received signal to generate a received sound spectrum, which is output to the response time calculating section 617 and the voice control section 621.

The response time calculating section 617, the hearing estimate section 619, and the voice control section 621 may have the functions described in the embodiments.

The IFFT section 623 applies a frequency-time transform to the received signal obtained from the voice control section 621, to transform the received signal into the received signal in the time domain.

The voice output section 625 is implemented with a D/A converter and a speaker 115 to apply a digital-analog conversion to the received signal obtain from the IFFT section 623. The received signal converted to an analog signal is output from the speaker 115 as the received sound.

In the modified example, although the example is explained in which the voice control device is implemented on a portable terminal device, it may be implemented on devices other than a portable terminal device. For example, each of the voice control devices described above or each of the voice control procedures described above is applicable to a TV telephone conference device and an information processing device having a telephone function.

Figure 26:
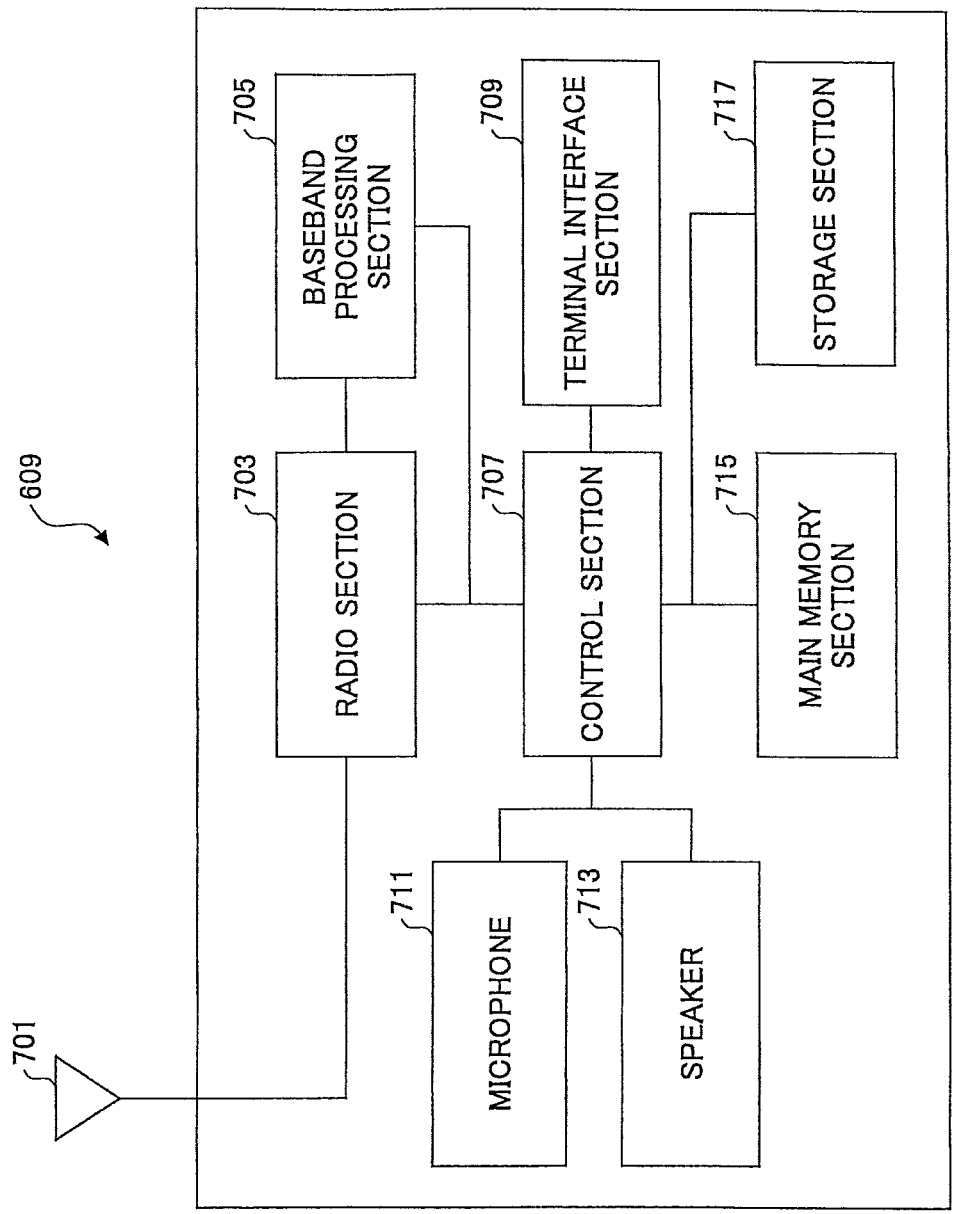
FIG. 26 is a block diagram illustrating an example of hardware of the portable terminal device according to the modified example.

FIG. 26 is a block diagram illustrating an example of hardware of the portable terminal device 609 according to the modified example. The portable terminal device 609 includes an antenna 701, a radio section 703, a baseband processing section 705, a control section 707, a terminal interface section 709, a microphone 711, a speaker 713, a main memory section 715, and an auxiliary storage section 717.

The antenna 701 sends a radio signal amplified by the sending amplifier, and receives a radio single sent from the base station. The radio section 703 applies a D/A conversion to the sending signal spread by the baseband processing section 705, converts it to a high frequency signal by a quadrature modulation, and amplifies the signal by a power amplifier. The radio section 703 amplifies the received radio signal and applies an A/D conversion to the amplified signal to send it to the baseband processing section 705.

The baseband section 705 executes various baseband processing such as an addition of error correcting codes to sending data, data modulation, spread modulation, despreading of a received signal, determination of receiving environment, determination of a threshold value for each channel signal, error correction decoding, etc.

The control section 707 executes radio control such as sending/receiving of a control signal. Also, the control section 707 executes the voice control program stored in the auxiliary storage section 717 to execute voice control according to the embodiments.

The main memory section 715 is a ROM (Read Only Memory), a RAM (Random Access Memory) or the like, which is a storage device to store or to temporarily store an OS, or the basic software executed by the control section 707, programs such as application software or the like, and data.

The auxiliary storage section 717 is an HDD (Hard Disk Drive) or the like, which is a storage device to store data related to the application software and the like. For example, the information illustrated in FIGS. 7 and 16 is stored in the auxiliary storage section 717.

The terminal interface section 709 executes adapter processing for data, and interface processing with a handset and an external data terminal.

This makes it possible to provide a voice in response to hearing of a user automatically during a call on the portable terminal device 609. Also, it is possible to implement the voice control device according to the embodiments as one or multiple semiconductor integrated circuits in the portable terminal device 609. Also, the disclosed technology can be implemented not only on the portable terminal device 609, but also on a fixed telephone and the like.

Also, it is possible to have a computer execute voice control described in the above embodiments by recording a program implementing voice control processing according to the above embodiments in a recording medium.

Also, it is possible to implement the above voice control processing by recording the program on a recording medium and having a computer or a portable terminal device read the recording medium on which the program is recorded. Here, various types of recording media can be used including a recording medium that records information optically, electrically, or magnetically such as a CD-ROM, a flexible disk, an optical magnetic disk and the like, and a semi-conductor memory and the like that records information electrically such as a ROM, a flash memory, and the like.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:
1. A voice control device inclusive of a semiconductor integrated circuit, comprising:
    a memory;
    a processor coupled to the memory and configured to:
        calculate a time length of a voice in a received signal;
        calculate a difference between a high range power and a low range power of the voice in the received signal as an articulation rate;
        calculate a response time representing a time difference between the voice in the received signal and a voice in a sending signal when the calculated time length of the voice in the received signal is longer than a first threshold value while the calculated articulation rate is greater than a third threshold;
        estimate hearing of a user based on the calculated response time;
        control the received signal by a compensation quantity depending on the estimated hearing; and
        produce sound responsive to the controlled received signal.
2. The voice control device as claimed in claim 1, wherein the processor is configured to:
    calculate a time length of the voice in the sending signal, and calculate the response time when the calculated time length of the voice in the sending signal is longer than a second threshold value.

3. The voice control device as claimed in claim 1, wherein the processor adjusts the compensation quantity depending on a time change in the response time to control the received signal using the adjusted compensation quantity.

4. The voice control device as claimed in claim 3, wherein the processor executes control to emphasize the received signal when the response time after the control is shorter than the response time before the control, or executes control to decrease the received signal when the response time after the control is longer than the response time before the control.

5. The voice control device as claimed in claim 1, wherein the processor does not calculate the response time when a starting time of the voice in the sending signal precedes an ending time of the voice in the received signal.

6. The voice control device as claimed in claim 1, wherein the processor estimates the hearing when the response time is less than a fourth threshold value.

7. The voice control device as claimed in claim 1, wherein the processor calculates an average response time by averaging a plurality of the calculated response times,
estimates the hearing based on the average response time.

8. A method of controlling voice in a voice control device inclusive of a semiconductor integrated circuit, comprising:
calculate a time length of a voice in a received signal;
calculate a difference between a high range power and a low range power of the voice in the received signal as an articulation rate;
calculating a response time representing a time difference between the voice in the received signal and a voice in a sending signal when the calculated time length of the voice in the received signal is longer than a first threshold value while the calculated articulation rate is greater than a third threshold;
estimating a hearing of a user based on the calculated the response time;
controlling the received signal by a compensation quantity depending on the estimated hearing; and
producing sound responsive to the controlled received signal.

9. A non-transitory computer-readable recording medium having a program stored therein for causing a computer to execute a method of controlling voice, the method comprising:
calculate a time length of a voice in a received signal;
calculate a difference between a high range power and a low range power of the voice in the received signal as an articulation rate;
calculating a response time representing a time difference between the voice in the received signal and a voice in a sending signal when the calculated time length of the voice in the received signal is longer than a first threshold value while the calculated articulation rate is greater than a third threshold;
estimating a hearing of a user based on the calculated the response time; and
controlling the received signal by a compensation quantity depending on the estimated hearing; and
producing sound responsive to the controlled received signal.

10. A portable terminal device, comprising:
a memory;
a processor coupled to the memory and configured to:
transform a received signal into a first spectrum;
transform a sending signal into a second spectrum;
calculate a time length of the first spectrum;
calculate a difference between a high range power and a low range power of the voice in the received signal as an articulation rate;
calculate a response time representing a time difference between the first spectrum and the second spectrum when the calculated time length of the voice in the received signal is longer than a first threshold value while the calculated articulation rate is greater than a third threshold;
estimate hearing of a user based on the calculated the response time;
control the first spectrum by a compensation quantity depending on the estimated hearing;
transform the controlled first spectrum into a controlled received signal; and
produce sound responsive to the controlled received signal.

* * * * *